(12) United States Patent
Imura

(10) Patent No.: US 7,502,099 B2
(45) Date of Patent: Mar. 10, 2009

(54) MEASURING METHOD AND APPARATUS FOR MEASURING AN OPTICAL PROPERTY OF A FLUORESCENT SAMPLE

(75) Inventor: Kenji Imura, Toyohashi (JP)

(73) Assignee: Konica Minolta Sensing, Inc., Osaka (JP)

( * ) Notice: Subject to any disclaimer, the term of this patent is extended or adjusted under 35 U.S.C. 154(b) by 41 days.

(21) Appl. No.: 11/398,911

(22) Filed: Apr. 6, 2006

(65) Prior Publication Data

US 2006/0227319 A1 Oct. 12, 2006

(30) Foreign Application Priority Data

Apr. 8, 2005 (JP) ............................ 2005-112336

(51) Int. Cl.
*G01N 21/00* (2006.01)
(52) U.S. Cl. .................... 356/72; 356/319; 356/402
(58) Field of Classification Search ............... 356/402, 356/319, 326, 317, 318, 417; 250/458.1–461.2; 702/189–199
See application file for complete search history.

(56) References Cited

U.S. PATENT DOCUMENTS 5,636,015 A * 6/1997 Imura et al. .................... 356/72
6,278,521 B1 * 8/2001 Jablonski et al. ............ 356/402

* cited by examiner

*Primary Examiner*—Gregory J. Toatley, Jr.
*Assistant Examiner*—Abdullahi Nur
(74) *Attorney, Agent, or Firm*—Brinks Hofer Gilson & Lione

(57) ABSTRACT

The method and the apparatus measures the total spectral radiance factor Bxs ($\lambda$) of a fluorescent sample illuminated by a specified illumination for testing Is without a fluorescent standard and a bothersome UV correction using it. The method and the apparatus calculates $Bxs(\lambda)$ based on the spectral intensity $Is(\lambda)$ of the illumination for testing, the measured spectral intensities $I1(\lambda)$ and $I2(\lambda)$ of actual illuminations I1 and I2 which are different from each other, a bi-spectral luminescent radiance factor $F(\mu,\lambda)$ or a bi-spectral radiance factor $B(\mu,\lambda)$ which is close to either of the sample, and the measured spectral intensities $Sx1(\lambda)$ and $Sx2(\lambda)$ of the light emitted from the sample illuminated by illuminations I1 and I2.

23 Claims, 12 Drawing Sheets

MEASURING METHOD AND APPARATUS FOR MEASURING AN OPTICAL PROPERTY OF A FLUORESCENT SAMPLE

This application is based on the application No. 2005-112336 filed in Japan, the contents of which are hereby incorporated by reference.

BACKGROUND OF THE INVENTION

1. Field of the Invention

The present invention relates to a method and an apparatus for measuring an optical property of a fluorescent sample.

2. Description of the Related Art

Today, paper and fabrics are often treated by FWA (Fluorescent Whitening Additives) and the effect of fluorescence to the observed whiteness or color of such products (referred to as "fluorescent sample" hereinafter) is not negligible. So that, method and an apparatus for measuring the optical property of those taking the effect of fluorescence into account is required.

Generally a visual property of a reflecting sample is expressed relatively to the perfect white and based on the total spectral radiance factor $B(\lambda)$ which is the ratio of light emitted from the sample to that from the perfect reflecting diffuser in the identical illuminating and receiving condition.

A color of fluoresced light is observed as a light source color alone, in case of a fluorescent sample, however, the fluoresced light is added to the reflected light and the color is observed as objective color. That is, the light emitted from the fluorescent sample is the sum of the reflected light and the fluoresced light, and accordingly the total spectral radiance factor $B(\lambda)$ of the fluorescent sample is also given as the sum of reflection spectral radiance factor $R(\lambda)$ and the fluorescent spectral radiance factor $F(\lambda)$ which are the ratios of light reflected and fluoresced from the sample respectively to the light reflected from the perfect reflecting diffuser in the identical illuminating and receiving condition as expressed by Equation 1.

$$B(\lambda)=R(\lambda)+F(\lambda) \quad (1)$$

Since the above mentioned perfect reflecting diffuser has no fluorescence and the reflectivity of which has no dependence on the wavelength, abovementioned total spectral radiance factor $B(\lambda)$, reflection spectral radiance factor $R(\lambda)$ and fluorescent spectral radiance factor $F(\lambda)$ are equivalent to the ratios of the light emitted, reflected and fluoresced from the sample respectively to the illumination light with a suitable proportional coefficient. The color of a fluorescent sample is observed as an objective color, and accordingly is related to the total spectral radiance factor $B(\lambda)$, from which the calorimetric values are derived.

CIE (International Committee of Illumination) defines spectral intensity distributions of several standard illuminations for colorimetry such as Illuminant D65, D50, D75 (daylight), Illuminant A (incandescent lamp), Illuminant F's, and Illuminant C. For the evaluation of fluorescent samples, Illuminant D65 or Illuminant C are generally used. The spectral excitation and fluorescence characteristics of fluorescent material is expressed by the Bi-spectral Luminescent Radiance Factor (referred to as "BLRF" hereinafter) $F(\mu,\lambda)$ which is the matrix data showing the intensity of the fluoresced light at wavelength $\lambda$ excited by monochromatic light of a unit intensity at wavelength $\mu$.

An example of abovementioned matrix data is shown in FIG. 8 where the cross-section along the fluorescence wavelength $\lambda$ expresses the spectral excitation efficiency for fluorescing at wavelength $\lambda$ while the cross-section along the excitation wavelength $\mu$ expresses the spectral intensity of fluoresced light excited at wavelength $\mu$. Accordingly, a sample containing fluorescent substance of the bi-spectral luminescent radiance factor $F(\mu,\lambda)$ has the fluorescent spectral radiance factor $F(\lambda)$ expressed by Equation (2), where the proportional coefficient is neglected, when illuminated by the light of the spectral intensity $I(\lambda)$.

$$F(\lambda)=F(\mu,\lambda)\cdot I(\mu)d\mu/I(\lambda) \quad (2)$$

That is $F(\lambda)$ is obtained as the ratio of convolution of the spectral intensity $I(\mu)$ of the illumination and the bi-spectral luminescent radiance factor $F(\mu,\lambda)$ to $I(\lambda)$.

As indicated by Equation (2), the fluorescent spectral radiance factor $F(\lambda)$ depends on the spectral intensity $I(\mu)$ of the illumination. Accordingly, the total spectral radiance factor $B(\lambda)$ being the sum of the reflection spectral radiance factor $R(\lambda)$ which itself doesn't depends on the spectral intensity $I(\mu)$ of the illumination and the fluorescent spectral radiance factor $F(\lambda)$, and the calorimetric values derived therefrom also depend on $I(\mu)$.

As the result, the spectral intensity $I(\mu)$ of the illumination (referred to as "illumination for testing" hereinafter) need to be specified when evaluating the optical property of a fluorescent sample and for the accurate measurement, the spectral intensity $I(\mu)$ of the illumination of a measuring apparatus need to be same as that of the specified illumination for testing. However, it is difficult and expensive to realize such an illumination of the same spectral intensity as that of standard illuminant D65 or C generally used as the illumination for testing.

Alternatively, the total spectral radiance factor $B(\lambda)$ or the fluorescent spectral radiance factor $F(\lambda)$ can be calculated using Equation (2) with the measured bi-spectral luminescent radiance factor $F(\mu,\lambda)$ or bi-spectral radiance factor $B(\mu,\lambda)$ of the sample and the spectral intensity $I(\mu)$ of the illumination for testing given as numerical data. Here, similarly to the bi-spectral luminescent radiance factor $F(\mu,\lambda)$, the bi-spectral radiance factor $B(\mu,\lambda)$ is the-matrix data showing the intensity of the total emission which is the sum of the fluoresced light at wavelength $\lambda$ excited by monochromatic light of a unit intensity at wavelength $\mu$ and the reflected light. The total spectral radiance factor $B(\lambda)$ is obtained as the ratio of the convolution of the spectral intensity $I(\mu)$ of the illumination and the bi-spectral radiance factor $B(\mu,\lambda)$ to the $I(\lambda)$.

$$B(\lambda)=\int B(\mu,\lambda)\cdot I(\mu)d\mu/I(\lambda) \quad (2\text{-}1)$$

However, since the measurement of the bi-spectral luminescent radiance factor $F(\mu,\lambda)$ or the bi-spectral radiance factor $B(\mu,\lambda)$ requires a complicated and expensive bi-spectro-fluorimeter comprising two spectral units, one for illumination and the other for receiving, and long time for measurement, this method is not practical. Quality controls of products treated by FWA such as paper are performed generally using either of two simplified methods mentioned below.

<Gaertner and Griesser's Method>

As shown in FIG. 10, fluorescent sample 601 is placed at sample aperture 603 of integrating sphere 602 of measuring apparatus 600 for measuring an optical property. Light source 604 such as Xe flash lamp contains sufficient UV component and the light flux 605 from it passes through the aperture and enters integrating sphere 602. A UV cut filter 606 is inserted so as to partially block the optical path of flux, and the flux which passes through the UV cut filter has the UV component eliminated. The degree of insertion of UV cur filter 606 is adjustable so as to allow adjustment of the UV intensity in the illumination light. Flux 605 partly passing through UV cut filter 606 and entering integrating sphere 602 undergoes diffuse reflection within the sphere and forms diffuse light which illuminates the fluorescent sample 601, and the radiant light 607 emitted in a predetermined direction from the illuminated surface passes through the observation aperture and enters sample spectral unit 608 which detects the spectral intensity $Sx(\lambda)$. Similarly, light flux 609 having the same intensity as the illumination light of fluorescent sample 601 enters monitoring optical fiber 610 so as to be directed to monitoring spectral unit 611 which detects the spectral intensity $Mx(\lambda)$. Controller 612 calculates the total spectral radiance factor $Bx(\lambda)$ from the spectral intensities $Sx(\lambda)$ and $Mx(\lambda)$ detected by spectral units 608 and 611.

A fluorescence standard containing fluorescent material having the excitation and fluorescence characteristics namely the bi-spectral luminescent radiance factor $F(\mu,\lambda)$ identical or similar to that of the sample to be measured and given a colorimetric value such as CIE whiteness under the specified illumination for testing is used to determine the degree of insertion of UV cut filter 606. The fluorescence standard is measured by measuring apparatus 600, and the UV intensity is corrected by adjusting the degree of insertion of UV cut filter 103 so as to match the value of CIE whiteness calculated from the obtained total spectral radiance factor $Bx(\lambda)$ to the CIE whiteness given to the fluorescence standard.

Gaertner and Griesser's method is mechanically complicated and unreliable, and also requires complicated and time-consuming operation, that is, measurements and movements of UV cut filter need to be repeated until the measured colorimetric value, CIE whiteness for example, agrees the given value. This method results the single specific colorimetric value, CIE whiteness in this case, compatible to that under specified illumination for testing, however from the principle, the multiple colorimetric values, the CIE whiteness and Tint value for example, or the total spectral radiance factor $Bx(\lambda)$ are not compatible simultaneously.

<Method of U.S. Pat. No. 5,636,015>

While Gaertner and Griesser's method modifies the UV content in the illumination first and modifies the total spectral radiance factor $Bx(\lambda)$ as the result, this method numerically synthesizes the total spectral radiance factor $Bx(\lambda)$ first and synthesizes the illumination of the spectral intensity necessary for the $Bx(\lambda)$ as the result. As shown in FIG. 11, integrating sphere 702 of measuring apparatus 700 is provided with a first illuminator 704 emitting light flux containing a UV component and a second illuminator 705 emitting light flux containing no UV component. Measuring apparatus 700 is further provided with a first spectral unit 709 detecting the spectral intensity of emitted light 708 from the fluorescent sample 701 placed at sample aperture 707 and a second spectral unit 712 detecting the spectral intensity of light 710 of the illumination conducted through optical fiber 711, and control unit 713. The fluorescent sample 701 is illuminated by first and second illuminators consecutively and the spectral intensities $Sx1(\lambda)$ and $Sx2(\lambda)$ of emitted light from said sample and the spectral intensities $Mx1(\lambda)$ and $Mx2(\lambda)$ of the illumination light are respectively detected. The total spectral radiance factors $Bx1(\lambda)$ and $Bx1(\lambda)$ corresponding to the illuminations by first and second illuminators are obtained from $Sx1(\lambda)$, $Sx2(\lambda)$, $Mx1(\lambda)$, and $Mx2(\lambda)$ and thus, the total spectral radiance factor $Bxc(\lambda)$ is synthesized by linearly combining $Bx1(\lambda)$ and $Bx2(\lambda)$ with the weight $W(\lambda)$ as shown in Equation (3)

$$Bxc(\lambda)=W(\lambda)\cdot Bx1(\lambda)+(1-W(\lambda))\cdot Bx2(\lambda) \qquad (3)$$

Similar to Gaertner and Griesser's method, abovementioned weight $W(\lambda)$ for each wavelength $\lambda$ is determined using a fluorescence standard containing fluorescent material having the excitation and fluorescence characteristics namely the bi-spectral luminescent radiance factor $F(\mu,\lambda)$ identical or similar to that of the sample to be measured and given a total spectral radiance factors $Bs(\lambda)$ under the specified illumination for testing. That is, weight $W(\lambda)$ is so determined for each wavelength $\lambda$ numerically that the synthesized total spectral radiance factor $Bxc(\lambda)$ by Equation (3) matches the given total spectral radiance factors $Bs(\lambda)$ under the specified illumination for testing.

This method is equivalent to respectively performing the correction of the UV content in the illumination by Gaertner and Griesser's method for the total spectral radiance factor $Bx(\lambda)$ at each wavelength as the target instead of the single colorimetric value. Since this method gives the total spectral radiance factors $Bxc(\lambda)$ of the sample comparable to $Bs(\lambda)$ under the specified illumination for testing, it has an advantage that all colorimetric values derived therefrom are also comparable to those under the specified illumination. Although this method eliminates many shortcomings of Gaertner and Griesser's method such as the mechanical complicacy, lack of reliability, and complicated and time-consuming operation, it still requires a fluorescence standard and errors due to the difference between the spectral intensity of the illumination at the time of UV correction and that at the time of sample measurement thereafter still remains.

If paper is treated by FWA, colors printed thereon are affected by fluorescence of the paper. Since the amount of excitation light reaching the paper substrate depends on the spectral transmittance of ink-covering the paper substrate, the spectral excitation-fluorescence characteristics (spectral excitation efficiency and spectral fluorescence intensity) of the printed paper depend on not only the spectral excitation-fluorescence characteristics of the paper but also on the spectral transmittance and the dot area (relative area covered by ink) of the ink on the area of paper. If paper is printed with two or more different inks, the paper is covered with those inks and the superposition of those, and accordingly, the spectral excitation-fluorescence characteristics of the measuring area depends on the spectral transmittance and the dot area of each of inks and the superposition of those.

Ink with the transmittance independent on wavelength doesn't change the relative spectral intensity of the illumination light reaching the paper substrate and equally influences to the spectral integrated excitation efficiency of the illumination synthesized by method of U.S. Pat. No. 5,636,015 and to that of the illumination for testing. Accordingly, the synthesized total, spectral radiance factor $Bxc(\lambda)$ of the printed paper is comparable to that to be obtained under the specified illumination for testing although they are different from those of unprinted paper. Here, the spectral integrated excitation efficiency $E(\lambda)$ expressed by Equation (4) is the excitation efficiency for fluorescence at wavelength excited by the whole illumination.

$$E(\lambda)=\int Q(\mu,\lambda)\cdot I(\mu)d\mu \qquad (4)$$

where $Q(\mu,\lambda)$ is the bi-spectral excitation efficiency, that is the excitation efficiency for fluorescence at wavelength $\lambda$ excited by light of a unit intensity and of bandwidth $d\mu$ at wavelength $\mu$.

As described above, both simplified methods (Gaertner and Griesser's method and method of U.S. Pat. No. 5,636,015) need the fluorescence standard. Since the fluorescence standard made of the same material as sample to be measured such as paper or fabric and containing the same fluorescent material as that contained in the sample is unstable and requires considerable cares for controlling the change due to the aging and for the renewal. Further, errors due to the change of the spectral intensity of the illumination after the UV correction is inevitable, and as the result, frequent UV readjustments are required for avoiding these errors. From these, a method and an apparatus for measuring fluorescent sample free from a fluorescence standard and a UV correction using the fluorescence standard are required.

Printing generally applies four primary inks (YMCK) on fluorescent paper and all inks except K (black) ink have the wavelength-dependent transmittances. That is, for most of printing material, abovementioned simplified methods do not provide an accurate colorimetric measurement taking the effect of fluorescence in account. Thus, a method and an apparatus for measuring printed colors on fluorescent paper taking not only the fluorescence of paper but also the spectral transmittance and the dot area of each of inks and the superposition of those in account are required. Said method and apparatus are further required to be free from a fluorescence standard and a UV correction.

The objective of the present invention is to provide a method and an apparatus for measuring the optical property of a fluorescent sample comparable to that under the specified illumination for testing without a fluorescence standard and a bothersome UV correction using the fluorescence standard.

SUMMARY OF THE INVENTION

To attain the above-mentioned object, a method for measuring an optical property of a fluorescent sample by obtaining a total spectral radiance factor of the sample illuminated by an illumination for testing, based on a bi-spectral radiance factor which is close to a bi-spectral radiance factor of the sample, a spectral intensity of the illumination for testing, spectral intensities of first and second illuminations which are different from each other, and measured spectral intensities of a light emitted from the sample illuminated by said first and second illuminations, said method comprising the steps of: calculating a spectral radiance factor by said illumination for testing based on said bi-spectral radiance factor and said spectral intensity of said illumination for testing; determining a weight at each wavelength so that a spectral radiance factor by a spectral intensity of a illumination synthesized by combination of said first and second illuminations weighted by said weight matches said spectral radiance factor by said illumination for testing; calculating a spectral intensity of a light emitted from the sample illuminated by said synthesized illumination based on said measured spectral intensities and weight; and calculating the total spectral radiance factor of the sample illuminated by said illumination for testing based on said spectral intensity by said synthesized illumination and a spectral intensity of said synthesized illumination.

BRIEF DESCRIPTION OF THE DRAWINGS

In the following description, like parts are designated by like reference numbers throughout the several drawings.

DETAILED DESCRIPTION OF THE PREFERRED EMBODIMENTS

Figure 1:
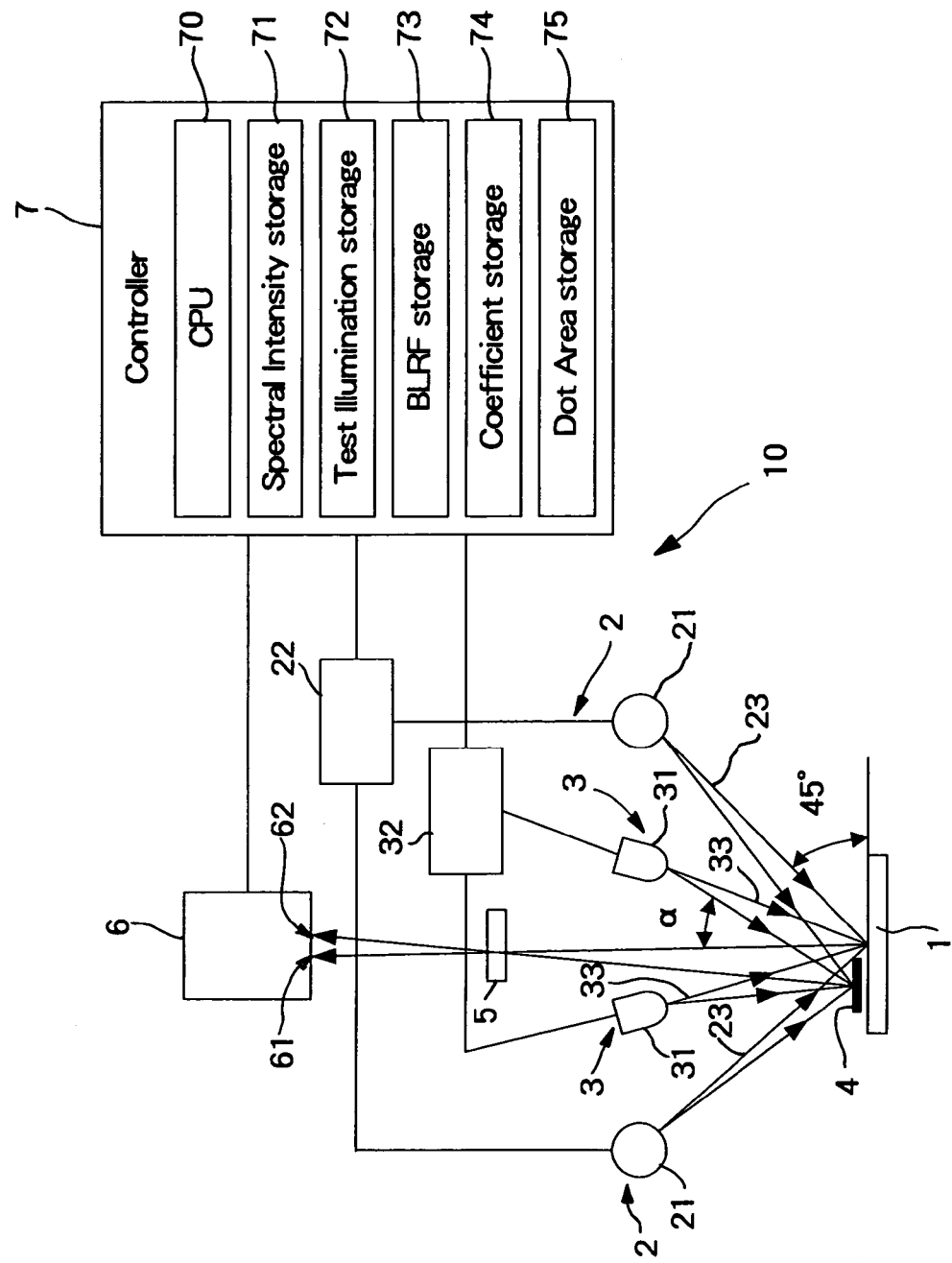
FIG. 1 illustrates the construction of an embodiment for the measuring method of the present invention.

FIG. 1 exemplarily shows the construction of the measuring apparatus for measuring the optical property of a fluorescent sample. As shown in FIG. 1, the measuring apparatus 10 comprises a sample 1 to be measured, a first illuminator 2, a second illuminator 3, a reference plane 4, a receiving optics 5, a dual channel spectral unit 6 and a controller 7. Sample 1 such as paper or fabrics containing FWA is placed at the sample position. First illuminator 2 for illuminating sample 1 comprises incandescent lamps 21 as the sources and a first driver 22 for driving said incandescent lamps 21. Second illuminator 3 for illuminating sample 1 comprises UV LED's 31 as the sources and a second driver 32 for driving said UV LED's 31. The source for second illuminator 3 is not limited to UV LED but can be any source emitting in UV region such as Xe flash lamp.

Reference plane 4 is a white and diffusively reflecting plane placed near the measuring area of sample 1. Receiving optics 5 is comprises a lens or lenses and receives light emitted from sample 1 and the reference plane 4 illuminated by said first and second illuminators and directs them into dual channel spectral unit 6 described later.

Dual channel spectral unit 6 performs spectral measurement of light incident from receiving optics 5. Dual channel spectral unit comprises a first incident slit 61 and a second incident slit 62. Light emitted from sample 1 and reference plane 4 illuminated by later-described illuminating light LA or LB are incident on first and second incident slits 61 and 62 respectively. Dual channel spectral unit 6 performs spectral measurement of the light emitted from sample 1 and passing through incident slit 61 to output the spectral intensity data as the first channel output and performs spectral measurement of the light emitted from reference plane 4, which is equivalent to the illumination light LA or LB, and passing through incident slit 62 to output the spectral intensity data as the second channel output.

Controller 7 comprises ROM (Read Only Memory) storing the control program and the like, RAM (Random Access Memory) storing data for processing, and CPU (Central Processing Unit) controlling all parts of measuring apparatus 10. Controller 7 controls the lighting of first and second illuminators 2 and 3 and measurement by dual channel spectral unit 6 and performs data processing for calculating the total spectral radiance factor of the fluorescent sample and for calibrating the relative spectral sensitivity described later.

When controller 7 turns on incandescent lamps 21 of first illuminator 2 via first driver 22, light flux 23 illuminates sample 1 from the direction of 45 degree off the normal of the sample. Similarly, when controller 7 turns on UV LED's 31 of second illuminator 3 via second driver 32, light flux 33 illuminates sample 1 from the direction closer to the normal than 45 degree.

Hereinafter, first illuminator is expressed by illuminator A and the combination of first and second illuminators is expressed by illuminator B. Light flux LA from illuminator A provided with incandescent lamps 21 has the negligible UV content while light flux LB from illuminator B provided with both incandescent lamps 21 and UV LED's 31 lit simultaneously has the sufficient UV content. Both illuminator A and B have the intensity in whole visible region that enables to calculate the radiance factor which is the ratio of the intensity of the light emitted from the sample relative to that emitted from the perfect reflecting diffuser in the identical illuminating and receiving condition for all visible wavelengths and accordingly enables to calculate the fluorescent spectral radiance factor or the total spectral radiance factor (radiance factors can not be calculated for the wavelength where the illumination has no intensity).

The near-normal component of the light emitted from sample 1 illuminated by the aforementioned light flux LA and LB are incident on first slit 61 and spectrally measured by dual channel spectral unit 6 and the respective spectral intensities of those $Sx1(\lambda)$ and $Sx2(\lambda)$ are sent to controller 7 as the first channel outputs. Similarly, the near-normal component of the light emitted from reference plane 4 simultaneously illuminated by the light flux LA and LB are incident on second slit 62 and spectrally measured by dual channel spectral unit 6 and the respective spectral intensities of those $Mx1(\lambda)$ and $Mx2(\lambda)$ are sent to controller 7 as the second channel outputs.

Figure 9:
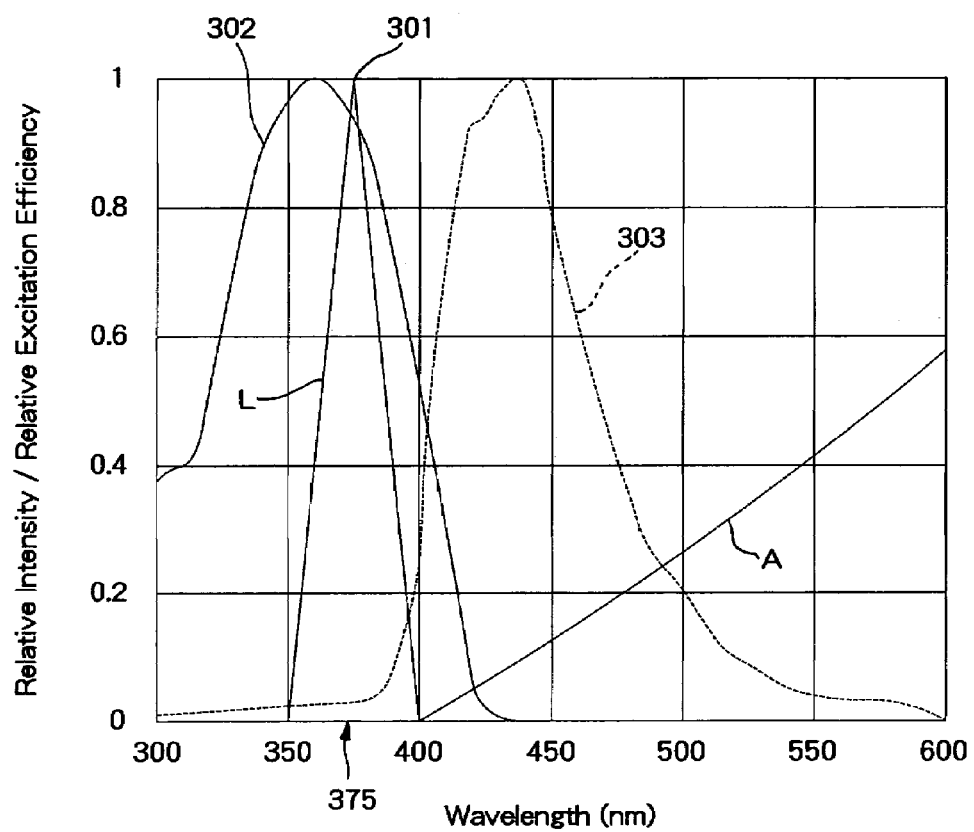
FIG. 9 shows spectral intensities of incandescent lamp and UV LED.
Figure 10:
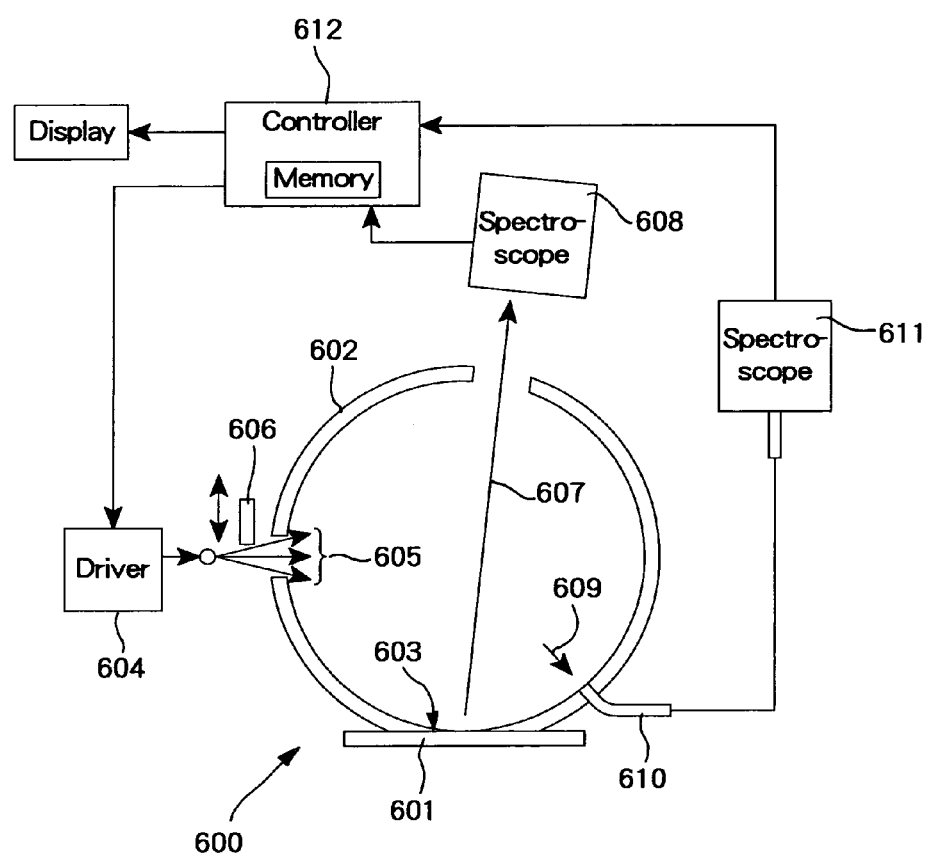
FIG. 10 shows the construction of a conventional measuring apparatus.
Figure 11:
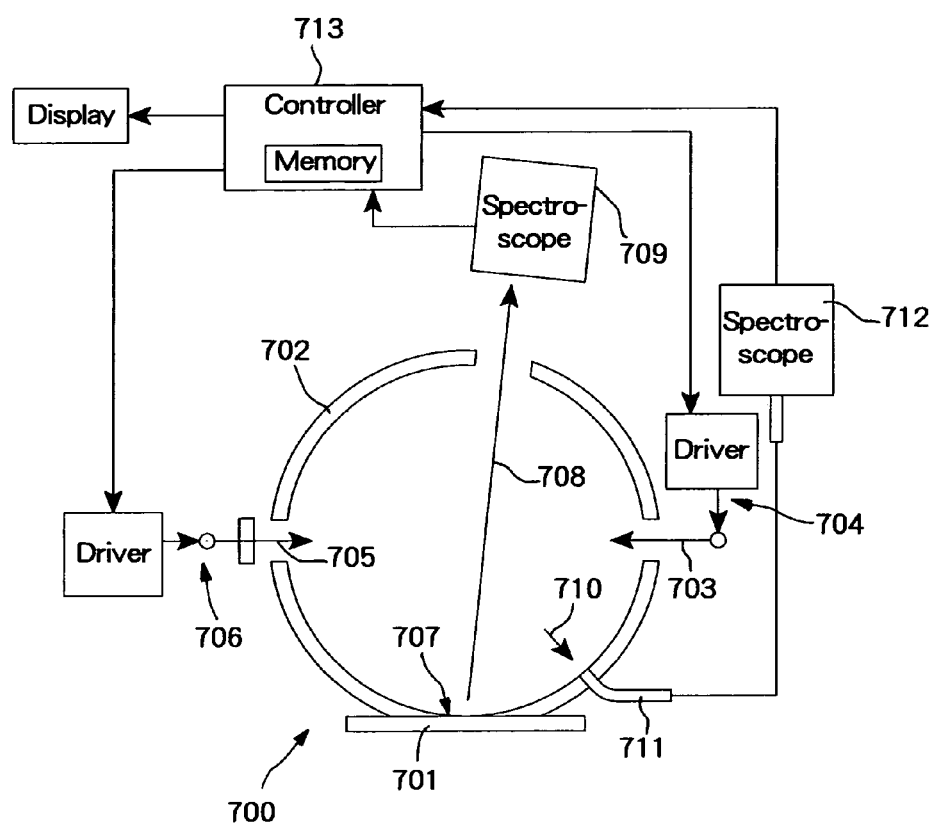
FIG. 11 shows the construction of a conventional measuring apparatus.

FIG. 9 exemplarily shows relative spectral intensities of typical incandescent lamp (A) and UV LED (L) together with a relative spectral excitation efficiency (302) and relative spectral fluorescence intensity (303) of typical FWA. As shown there, center wavelength 301 (around 375 nm) of the spectral intensity of the UV LED (L) is near the wavelength giving the peak excitation efficiency.

Since the method of the this embodiment needs to thoroughly know the spectral intensity of the illumination light in the excitation wavelength range of FWA, dual channel spectral unit 6 has the measurable wavelength range covering the emission wavelength range of the UV LED, from 360 to 740 nm for example. Illuminations by incandescent lamp and UV LED are free from a triplet effect which happens when a fluorescent sample is illuminated by very strong light for a very short duration like the case of Xe flash light source. The triplet effect is light absorption caused by an unusual transition from the singlet to the triplet electronic state of molecule and is problematic as it damages the compatibility of measurement to the visual appearance.

The illumination and receiving system of measuring apparatus 10 forms 45/0 geometry which is one of standard geometries for colorimetric measurement of a reflective sample. The purpose of the geometry is to control the specularly reflected light from the sample surface, however the position of second illuminator 3 (UV LED's) is free from the requirements of the geometry because the specular reflection of the UV emission has no influence to a colorimetric property.

As shown in FIG. 1, controller 7 comprises a CPU 70, a spectral intensity storage 71, a test illumination storage 72, a BLRF storage 73, a coefficient storage 74 and a dot area storage 75. CPU 70 performs the control of first and second illuminators 2 and 3 and dual channel spectral unit 6 and performs the data processing for the total spectral radiance factor of the fluorescent sample and for the calibration of the relative spectral sensitivity. Spectral intensity storage 71 stores the spectral intensity data of the light emitted from sample 1 and reference plane 4 measured and sent by dual channel spectral unit 6. Test illumination storage 72 stores the spectral intensity data of the illumination for testing (hereinafter referred to as "test illumination") given in advance. BLRF data storage 73 stores the bi-spectral luminescent radiance factor (hereinafter referred to as "BLRF") data which is identical or similar to that of the sample to be measured and given in advance.

Coefficient storage 74 stores the sensitivity calibration coefficient for calibrating the relative spectral sensitivity of dual channel spectral unit 6, the conversion coefficient for converting the spectral intensity of the light reflected by reference plane 4 (hereinafter referred to as "reference light") to the spectral intensity of the light illuminating sample 1 (hereinafter referred to as "sample illumination"), and the calibration coefficient for deriving the total spectral radiance factor of sample 1 from the spectral intensity of the light emitted from the sample (hereinafter referred to as "sample light") and that of the reference light. Dot area storage 75 stores dot area data for each of inks and the superposition of those for measuring printed fluorescent material.

Controller 7 performs calculation for (A) a total spectral radiance factor under a specified illumination for testing and (B) a total spectral radiance factor of a printed surface on paper treated by FWA, based on the spectral intensity data of the sample and reference light, the bi-spectral luminescent radiance factor, the sensitivity calibration coefficient, the conversion coefficient, and the calibration coefficient.

(A) A Total Spectral Radiance Factor Under a Specified Illumination for Testing

<Principle of Measurement>

In principle, for obtaining the total spectral radiance factor of a fluorescent sample under a specified illumination for testing, a bi-spectro-fluorimeter or a measuring apparatus provided with the illumination whose spectral intensity is close to that of the illumination for testing is required. Differently, this embodiment of the present invention numerically synthesizes the virtual illumination presenting the identical fluorescent spectral radiance factor to that presented by the specified illumination for testing for the fluorescent sample having the excitation-fluorescence property close to that of the specific bi-spectral luminescent radiance factor. That is, the virtual illumination Ic is synthesized by linearly combining two different illuminations I1 and I2 with the suitable weight so that the fluorescent spectral radiance factor $Fc(\lambda)$ by the synthesized illumination Ic given by Equation (2) matches $Fs(\lambda)$ by the illumination for testing Is. Here, the spectral intensities $I1(\lambda)$ and $I2(\lambda)$ of the illuminations I1 and I2 are different specially in the relative intensities between visible and UV regions. Thus, Ic is so synthesized that the spectral intensity $Ic(\lambda)$ satisfies Equation (5), where $Is(\lambda)$ is the spectral intensity of the specified illumination for testing and $F(\mu,\lambda)$ is the specific bi-spectral luminescent radiance factor.

$$\int F(\mu,\lambda) \cdot Is(\mu) d\mu / Is(\lambda) = \int F(\lambda,\mu) \cdot Ic(\mu) d\mu / Ic(\lambda) \tag{5}$$

$I1(\lambda)$ and $I2(\lambda)$ are linearly combined with the wavelength-dependent weights $W(\lambda)$ and $(1-W(\lambda))$ as expressed by Equation (6).

$$Ic(\lambda) = W(\lambda) \cdot I1(\lambda) + (1-W(\lambda)) \cdot I2(\lambda) \tag{6}$$

Thus, the fluorescent spectral radiance factor $Fc(\lambda)$ by the synthesized illumination Ic is given by Equation (7).

$$Fc(\lambda)=\int F(\mu,\lambda)\cdot Ic(\mu)d\mu/Ic(\lambda)=\int F(\mu,\lambda)\cdot(W(\lambda)\cdot I1(\mu)+(1-W(\lambda))\cdot I2(\mu))d\mu/(W(\lambda)\cdot I1(\lambda)+(1-W(\lambda))\cdot I2(\lambda)) \quad (7)$$

Accordingly, Equation (5) is rewritten to Equation (8).

$$\int F(\mu,\lambda)\cdot Is(\mu)d\mu/Is(\lambda)=\int F(\mu,\lambda)\cdot(W(\lambda)\cdot I1(\mu)+(1-W(\lambda))\cdot I2(\mu))d\mu/(W(\lambda)\cdot I1(\lambda)+(1-W(\lambda))\cdot I2(\lambda)) \quad (8)$$

Thus, the weight $W(\lambda)$ is determined based on Equation (8) with the bi-spectral luminescent radiance factor $F(\mu,\lambda)$, spectral intensities of the illumination for testing $Is(\lambda)$ and actual illuminations $I1(\lambda)$ and $I2(\lambda)$. $F(\mu,\lambda)$ and $Is(\lambda)$ are given and stored as numerical data in advance and $I1(\lambda)$ and $I2(\lambda)$ are obtained from measured spectral intensities of reference light. Thus, the total spectral radiance factor $Bxs(\lambda)$ of the fluorescent sample having the bi-spectral luminescent radiance factor close to that used for determining the weight $W(\lambda)$ and illuminated by the illumination for testing is calculated using weight $W(\lambda)$. For this, spectral intensities $Sx1(\lambda)$ and $Sx2(\lambda)$ of the light emitted from the sample illuminated by illuminations I1 and I2 and spectral intensities $I1(\lambda)$ and $I2(\lambda)$ of illuminations I1 and I2 are linearly combined respectively with the weights $W(\lambda)$ and $(1-W(\lambda))$ obtained above as shown by Equations (9) and (10), where $Sxc(\lambda)$ is the spectral intensity of the light emitted from the sample virtually illuminated by the synthesized illumination Ic and $Ic(\lambda)$ is the spectral intensity of Ic.

$$Sxc(\lambda)=W(\lambda)\cdot Sx1(\lambda)+(1-W(\lambda))\cdot Sx2(\lambda) \quad (9)$$

$$Ic(\lambda)=W(\lambda)\cdot I1(\lambda)+(1-W(\lambda))\cdot I2(\lambda) \quad (10)$$

Then, the total spectral radiance factor $Bxs(\lambda)$ is obtained from $Sxc(\lambda)$, $Ic(\lambda)$ and the calibration coefficient $C(\lambda)$ by Equations (11).

$$Bxs(\lambda)=C(\lambda)\cdot Sxc(\lambda)/Ic(\lambda) \quad (11)$$

The procedures mentioned above can be simplified when both of illumination I1 and I2 have the intensities in visible region as in the case of this embodiment where the illuminations I1 and I2 are respectively illuminations LA and LB. In this simplified procedure, as many pairs of virtual illuminations having the spectral intensities $I1_\lambda(\mu)=I1(\mu)/I1(\lambda)$ and $I2_\lambda(\mu)=I2(\mu)/I2(\lambda)$ as the number of wavelengths $\lambda$ in visible region are introduced. Each $I1_\lambda(\mu)$ and $I2_\lambda(\mu)$ for each wavelength $\lambda$ are given as the relative spectral intensities to the intensities at wavelength $\lambda$, $I1(\lambda)$ and $I2(\lambda)$, in visible region and are different at different wavelength. From the definition of $I1_\lambda(\mu)$ and $I2^\lambda(\mu)$, $I1_\lambda(\lambda)=1$ and $I2_\lambda(\lambda)=1$. With $I1_\lambda(\mu)$ and $I2_\lambda(\mu)$ introduced above, the denominator in right side of Equation (8) becomes $(W(\lambda)\cdot I1(\lambda)+(1-W(\lambda))\cdot I2(\lambda))$ and always equals to 1. Accordingly Equation (7) is rewritten to Equation (12) and the fluorescent spectral radiance factor $Fc(\lambda)$ by the synthesized illumination Ic is given by linearly combining the fluorescent spectral radiance factor $F1(\lambda)$ and $F2(\lambda)$ under the illumination I1 and I2.

$$\int F(\mu,\lambda)\cdot Ic(\mu)d\mu/Ic(\lambda)=W(\lambda)\cdot\int F(\mu,\lambda)\cdot I1_\lambda(\mu)d\mu+(1-W(\lambda))\cdot\int F(\mu,\lambda)\cdot I2_\lambda(\mu)d\mu=W(\lambda)\cdot\int F(\mu,\lambda)\cdot I1(\mu)d\mu/I1(\lambda)+\int F(\mu,\lambda)\cdot((1-W(\lambda))\cdot I2(\mu)d\mu/I2(\lambda) \quad (12)$$

Thus, Equation (5) is rewritten to Equation (13).

$$\int F(\mu,\lambda)\cdot Is(\mu)d\mu/Is(\mu)=W(\lambda)\cdot\int F(\mu,\lambda)\cdot I1(\mu)d\mu/I1(\mu)+(1-W(\lambda))\cdot\int F(\mu,\lambda)\cdot I2(\mu))d\mu/I2(\lambda)) \quad (13)$$

Equation (12) indicates that the fluorescent spectral radiance factor $Fc(\lambda)$ can be obtained by the illumination $Ic_\lambda(\mu)$ synthesized for each wavelength in visible region by linearly combining two virtual illuminations $I1_\lambda(\mu)=I1(\mu)/I1(\lambda)$ and $I2_\lambda(\mu)=I2(\mu)/I2(\lambda)$ introduced above with the weights $W(\lambda)$ and $(1-W(\lambda))$ as shown in Equation (12').

$$Ic_\lambda(\mu)=W(\lambda)\cdot I1(\mu)/I1(\lambda)+(1-W(\lambda))\cdot I2(\mu)/I2(\lambda) \quad (12')$$

Similar to the case of Equation (8) mentioned before, the weight $W(\lambda)$ can be determined based on Equation (13) with the bi-spectral luminescent radiance factor $F(\mu,\lambda)$, spectral intensities of the illumination for testing $Is(\lambda)$ and actual illuminations $I1(\lambda)$ and $I2(\lambda)$.

The method of U.S. Pat. No. 5,636,015 is differently understood that it replaces the integration in right side of Equation (13) by the actually measuring the total spectral radiance factor of a fluorescence standard since the spectral intensities $I1(\lambda)$ and $I2(\lambda)$ of the actual illuminations are unknown in said method.

Thus, the fluorescent spectral radiance factor $Fxc(\lambda)$ of the fluorescent sample having the bi-spectral luminescent radiance factor $F(\mu,\lambda)$ close to that used for determining the weight $W(\lambda)$ and virtually illuminated by the synthesized illumination Ic is expressed by Equation (14) with the fluorescent spectral radiance factors $Fx1(\lambda)$ and $Fx2(\lambda)$ under the actual illuminations I1 and I2 (illuminations LA and LBI2) and the weight $W(\lambda)$ determined by Equation (13).

$$Fxc(\lambda)=W(\lambda)\cdot Fx1(\lambda)+(1-W(\lambda))\cdot Fx2(\lambda) \quad (14)$$

Accordingly, the total spectral radiance factor $Bxc(\lambda)$ being the sum of the fluorescent spectral radiance factor $Fxs(\lambda)$ and the reflection spectral radiance factor $Rxs(\lambda)$ can be obtained by linearly combining the total spectral radiance factors $Bx1(\lambda)$ and $Bx2(\lambda)$ measured by illuminating the sample by the illuminations I1 and I2 with the weights $W(\lambda)$ and $(1-W(\lambda))$ as shown by Equation (15).

$$Bxc(\lambda)=W(\lambda)\cdot Bx1(\lambda)+(1-W(\lambda))\cdot Bx2(\lambda) \quad (15)$$

Although the weight $W(\lambda)$ is determined based on Equation (8) or (15) based on the bi-spectral luminescent radiance factor $F(\mu,\lambda)$, the $W(\lambda)$ can be also determined based on the bi-spectral total radiance factor $B(\mu,\lambda)$ using Equation (8) or (15) in which $F(\mu,\lambda)$ is replaced by $B(\mu,\lambda)$ since $Bc(\lambda)=Bs(\lambda)$ if $Fc(\lambda)=Fs(\lambda)$.

Hereinafter two calibrations necessary for the measurement of a fluorescent sample in this embodiment are described.

<1. Calibration of the Relative Sensitivity of the Spectral Unit>

In the method mentioned above, spectral intensities of the actual illuminations need to be known and for this, the relative spectral sensitivity of the spectral measurement unit for the sample light (first channel of the dual channel spectral unit in this embodiment) is calibrated in advance at the time of production for example. First, the wavelength calibration is performed to the spectral measurement unit using a known art, and a light source of the known spectral intensity distribution $A(\lambda)$ such as A illuminant is measured to get the output $Sa(\lambda)$ from the spectral measurement means. The sensitivity calibration coefficient $G(\lambda)$ is given by Equation (16).

$$G(\lambda)=A(\lambda)/Sa(\lambda) \quad (16)$$

<2. White Calibration>

In the white calibration prior to the sample measurement, a fluorescence-free white calibration standard of the known reflection spectral radiance factor $Rw(\lambda)$ is positioned at the sample position, illuminated by the illuminations I1 and I2 (illumination LA and LB), and the spectral intensities $Sw1(\lambda)$ and $Sw2(\lambda)$ of the sample light and the spectral intensities Mw1($\lambda$) and Mw2($\lambda$) of the reference light are measured respectively. And, two coefficients described in following (1) and (2) are derived.

(1) Conversion coefficients D1($\lambda$) and D2($\lambda$) for converting the spectral intensities Mx1($\lambda$) and Mx2($\lambda$) of the reference light to the spectral intensities I1($\lambda$) and I2($\lambda$) of the sample illumination The conversion coefficients D1($\lambda$) and D2($\lambda$) for converting the spectral intensities Mx1($\lambda$) and Mx2($\lambda$) of the reference light at the time of sample measurement to the spectral intensities I1($\lambda$) and I2($\lambda$) of the sample illumination are derived by Equations (17) and (18) using spectral intensities Sw1($\lambda$) and Sw2($\lambda$) of the sample light and spectral intensities Mw1($\lambda$) and Mw2($\lambda$) of the reference light when the white calibration standard of the reflection spectral radiance factor Rw($\lambda$) is illuminated by the illumination I1 and I2 and the sensitivity calibration coefficient G($\lambda$) given by Equation (16).

$$D1(\lambda) = G(\lambda) \cdot Sw1(\lambda) / (Mw1(\lambda) \cdot Rw(\lambda)) \quad (17)$$

$$D2(\lambda) = G(\lambda) \cdot Sw2(\lambda) / (Mw2(\lambda) \cdot Rw(\lambda)) \quad (18)$$

Thus, the spectral intensities Mx1($\lambda$) and Mx2($\lambda$) of the reference light at the time of sample measurement are converted to the spectral intensities I1($\lambda$) and I2($\lambda$) of the sample illumination using the conversion coefficients D1($\lambda$) and D2($\lambda$) by Equations (19) and (20).

$$I1(\lambda) = D1(\lambda) \cdot Mx1(\lambda) \quad (19)$$

$$I2(\lambda) = D2(\lambda) \cdot Mx2(\lambda) \quad (20)$$

(2) Calibration coefficients C1($\lambda$) and C2($\lambda$) for deriving the total spectral radiance factors Bx1($\lambda$) and Bx2($\lambda$) from the spectral intensities Sx1($\lambda$) and Sx2($\lambda$) of the sample light and the spectral intensities Mx1($\lambda$) and Mx2($\lambda$) of the reference light when the sample is illuminated by illuminations I1 and I2.

The calibration coefficients C1($\lambda$) and C2($\lambda$) are derived by Equations (21) and (22) using the spectral intensities Sw1($\lambda$) and Sw2($\lambda$) of the sample light and the spectral intensities Mw1($\lambda$) and Mw2($\lambda$) of the reference light when the white calibration standard of the reflection spectral radiance factor Rw($\lambda$) is illuminated by the illuminations I1 and I2.

$$C1(\lambda) = Rw(\lambda) / (Sw1(\lambda) / Mw1(\lambda)) \quad (21)$$

$$C2(\lambda) = Rw(\lambda) / (Sw2(\lambda) / Mw2(\lambda)) \quad (22)$$

Thus, the total spectral radiance factors Bx1($\lambda$) and Bx2($\lambda$) are derived from the spectral intensities Sx1($\lambda$) and Sx2($\lambda$) of the sample light and the spectral intensities Mx1($\lambda$) and Mx2($\lambda$) of the reference light when the sample is illuminated by the illuminations I1 and I2 using the calibration coefficients C1($\lambda$) and C2($\lambda$) by Equations (23) and (24).

$$Bx1(\lambda) = C1(\lambda) \cdot Sx1(\lambda) / Mx1(\lambda) \quad (23)$$

$$Bx2(\lambda) = C2(\lambda) \cdot Sx2(\lambda) / Mx2(\lambda) \quad (24)$$

The principle of the measuring method of the total spectral radiance factor of a fluorescent sample mentioned above can be summarized as below.

A1. The spectral property of the fluorescent light from the illuminated fluorescent sample is obtained from the spectral intensity of the illumination and the bi-spectral luminescent radiance factor of the sample (Equation (2)).

A2. Accordingly, by knowing the spectral intensity of the illumination, the total spectral radiance factor of the virtual fluorescence standard having the known bi-spectral luminescent radiance factor can be calculated and the actual fluorescence standard of conventional (simplified) methods can be replaced by the virtual fluorescence standard.

A3. Method of U.S. Pat. No. 5,636,015 is applied with the virtual fluorescence standard.

A4. The spectral intensity of the illumination for testing is given as numerical data in advance and those of the actual illuminations for measurement are actually measured.

<Procedures for Measuring the Total Spectral Radiance Factor of a Fluorescent Sample>

Figure 3:
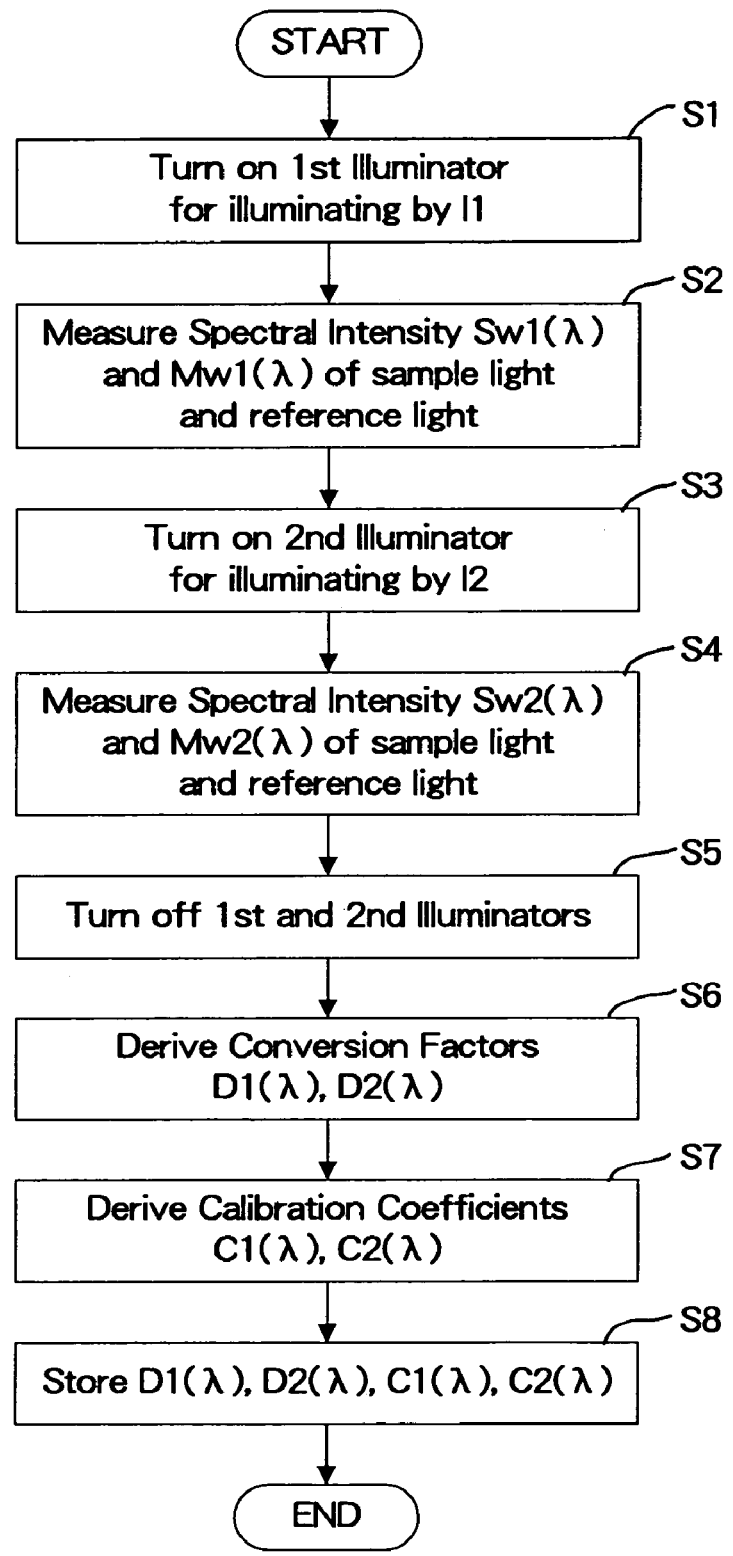
FIG. 3 shows a flowchart for white calibration of the measuring method of the present invention.

Procedures for measuring the total spectral radiance factor Bxs($\lambda$) of a fluorescent sample by measuring apparatus 10 comprises the procedure for white calibration performed in advance and the procedure for sample measurement performed thereafter. FIG. 3 exemplarily shows a flowchart for the white calibration. As shown there, controller 7 turns on first illuminator 2 (incandescent lamps 21) to illuminate the fluorescence-free white calibration standard whose reflectance spectral radiation factor Rw($\lambda$) is known by the illumination light LA (illumination light I1) (Step S1), and the spectral intensity Sw1($\lambda$) of the sample light, which is the reflected light in case of the fluorescence-free white calibration standard, by said illumination LA is measured. Simultaneously, the spectral intensity Mw1($\lambda$) of the illumination light LA is measured and the spectral intensity data Sw1($\lambda$) and Mw1($\lambda$) are stored in spectral intensity storage 71 (Step S2).

After that, controller 7 turns on second illuminator 3 (UV LED's 31) keeping first illuminator 2 on as in step S1 to illuminate the calibration standard by the illumination LB (illumination light I2) by both first and second illuminators (Step S3), and the spectral intensity Sw2($\lambda$) of the sample light by said illumination LB is measured. Simultaneously, the spectral intensity Mw2($\lambda$) of the illumination light LB is measured and the spectral intensity data Sw2($\lambda$) and Mw2($\lambda$) are stored in spectral intensity storage 71 (Step S4). Then, both first and second illuminators are turned off (Step S5).

Then, the conversion coefficients D1($\lambda$) and D2($\lambda$) for converting the spectral intensities Mx1($\lambda$) and Mx2($\lambda$) of the reference light at the time of sample measurement to the spectral intensities I1($\lambda$) and i2($\lambda$) of the sample illumination are derived by Equations (17) and (1 8) using the spectral intensities Sw1($\lambda$) and Sw2($\lambda$) of the sample light, the spectral intensities Mw1($\lambda$) and Mw2($\lambda$) of the reference light, the sensitivity calibration coefficient G($\lambda$) given by Equation (16), and the reflectance spectral radiation factor Rw($\lambda$) of the white calibration standard (Step S6).

Further the calibration coefficients C1($\lambda$) and C2($\lambda$) are derived by Equations (21) and (22) using the spectral intensities Sw1($\lambda$) and Sw2($\lambda$) of the sample light, the spectral intensities Mw1($\lambda$) and Mw2($\lambda$) of the reference light, and the known reflection spectral radiance factor Rw($\lambda$) (Step S7). And the conversion coefficients D1($\lambda$) and D2($\lambda$) and the calibration coefficients C1($\lambda$) and C2($\lambda$) are stored in coefficients storage 74 (Step S8).

Figure 4:
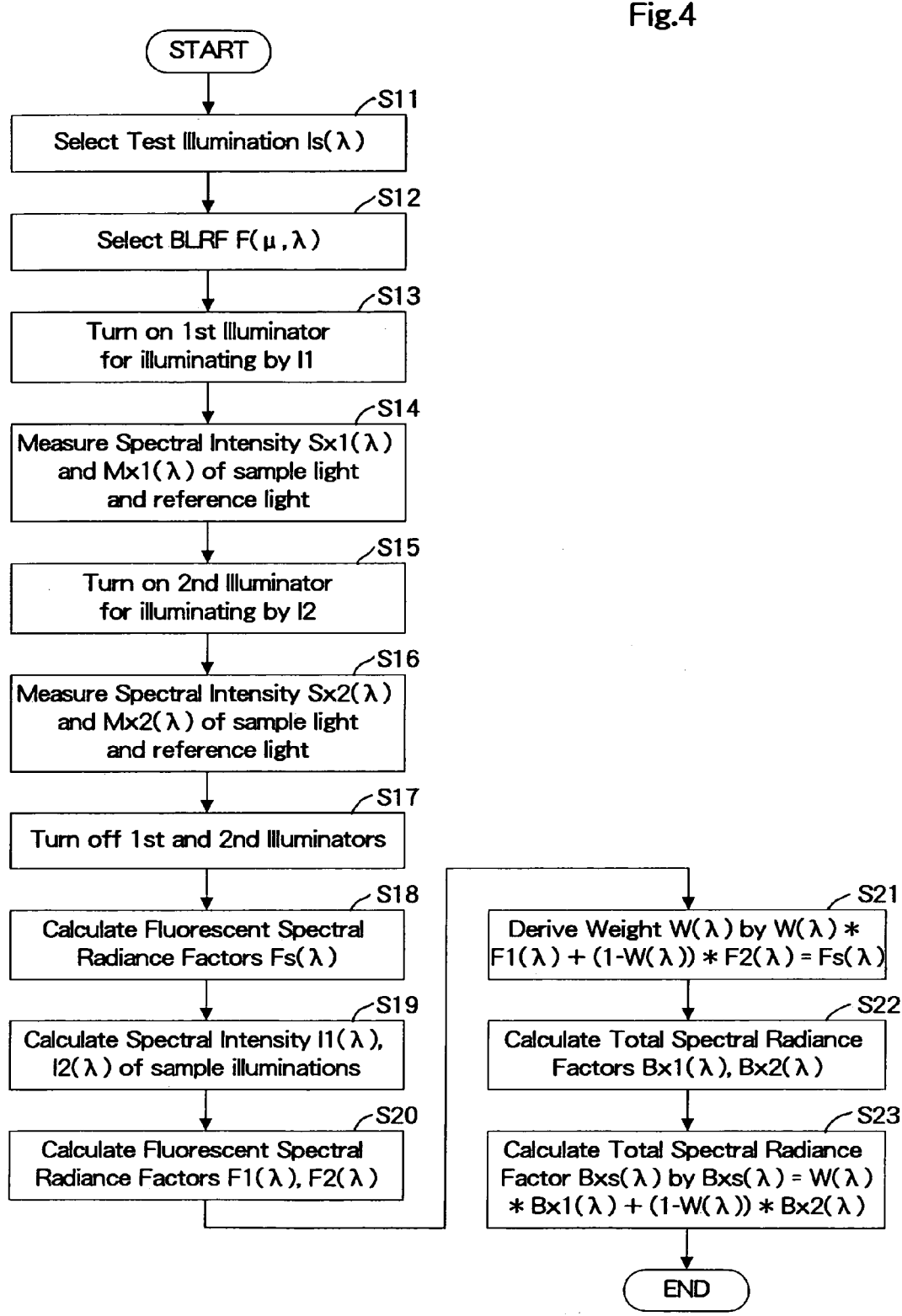
FIG. 4 shows a flowchart for measuring a fluorescent sample by the measuring method of the present invention.

FIG. 4 exemplarily shows a flowchart for measuring the total spectral radiance factor of a fluorescent sample. As shown there, first, a test illumination Is is selected. That is controller 7 reads out the spectral intensity data Is($\lambda$)=Is($\mu$) of the selected test illumination from test illumination storage 72 (Step S11). Next, the type of the sample to be measured is selected. That is controller 7 reads out the bi-spectral fluorescent radiance factor data F($\mu,\lambda$) which is close to that of the sample from BLRF storage 73 (Step S12). Next, controller 7 turns on first illuminator 2 (incandescent lamps 21) to illuminate the sample by the illumination light LA (illumination light I1) (Step S13), and the spectral intensity $Sx1(\lambda)$ of the sample light by the illumination light LA is measured by dual channel spectral unit 6. Simultaneously, the spectral intensity $Mx1(\lambda)$ of the illumination light LA is measured and the spectral intensity data $Sx1(\lambda)$ and $Mx1(\lambda)$ are stored in spectral intensity storage 71 (Step S14).

After that, controller 7 turns on second illuminator 3 (UV LED's 31) keeping first illuminator 2 on as step S13 to illuminate the sample by the illumination light LB (illumination light I2) by both first and second illuminators (Step S15), and the spectral intensity $Sx2(\lambda)$ of the sample light by the illumination light LB is measured. Simultaneously, the spectral intensity $Mx2(\lambda)$ of the illumination light LB is measured and the spectral intensity data $Sx2(\lambda)$ and $Mx2(\lambda)$ are stored in spectral intensity storage 71 (Step S16). Then, both first and second illuminators are turned off (Step S17).

Next, controller 7 calculates the fluorescent spectral radiance factor $Fs(\lambda)$ by the selected test illumination Is by Equation (25) using the spectral intensity data $Is(\lambda)=Is(\mu)$ and the bi-spectral luminescent radiance factor data $F(\mu,\lambda)$ read out in steps S11 and S12 (Step S18).

$$Fs(\lambda)=\int F(\mu,\lambda)\cdot Is(\mu)d\mu/Is(\lambda) \qquad (25)$$

Then, controller 7 converts the spectral intensities $Mx1(\lambda)$ and $Mx2(\lambda)$ of the reference light to the spectral intensities $I1(\lambda)$ and $I2(\lambda)$ of the sample illumination (LA and LB) by Equations (19) and (20) (Step S19) and calculates the fluorescent radiance factors $F1(\lambda)$ and $F2(\lambda)$ by the illuminations LA and LB (I1 and I2) by Equations (26) and (27) using the $I1(\lambda)=I1(\mu)$ and $I2(\lambda)=I2(\mu)$ obtained above and the bi-spectral luminescent radiance factor data F(82 ,$\lambda$) (Step S20).

$$F1(\lambda)=\int F(\mu,\lambda)\cdot I1(\mu)d\mu/I1(\lambda) \qquad (26)$$

$$F2(\lambda)=\int F(\mu,\lambda)\cdot I2(\mu)d\mu/I2(\lambda) \qquad (27)$$

Next, controller 7 derives the weight $W(\lambda)$ for each wavelength by solving Equation (28) including the fluorescent spectral radiance factors $F1(\lambda)$ and $F2(\lambda)$ calculated above and the $Fs(\lambda)$ calculated in step S18 (Step S21).

$$W(\lambda)\cdot F1(\lambda)+(1-W(\lambda))\cdot F2(\lambda)=Fs(\lambda) \qquad (28)$$

Then, controller 7 calculates the total spectral radiance factors $Bx1(\lambda)$ and $Bx2(\lambda)$ of the sample under the illumination LA and LB (I1 and I2) by Equation (23) and (24) using $Mx1(\lambda)$ and $Mx2(\lambda)$ stored in steps S14 and S16 (Step S22), and calculates the total spectral radiance factor $Bs(\lambda)$ under the test illumination by Equation (29) using $Bx1(\lambda)$ and $Bx2(\lambda)$ calculated and the weights $W(\lambda)$ obtained in step S21 (Step S23).

$$Bxs(\lambda)=W(\lambda)\cdot Bx1(\lambda)+(1-W(\lambda))\cdot Bx2(\lambda) \qquad (29)$$

(B) A Total Spectral Radiance Factor of a Printed Surface on Paper Treated by FWA <Principle of Measurement>

Figure 12A:
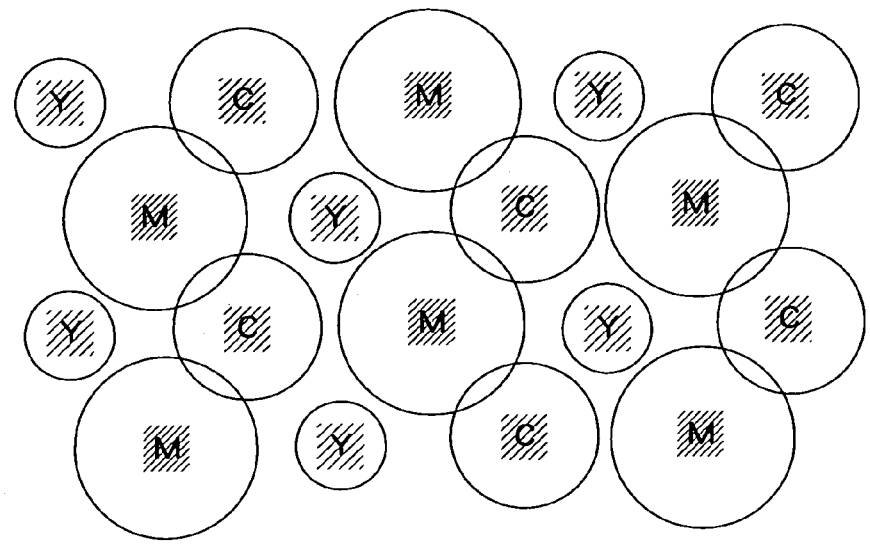
FIG. 12 explains ink dots and superposition of those on paper.
Figure 12B:
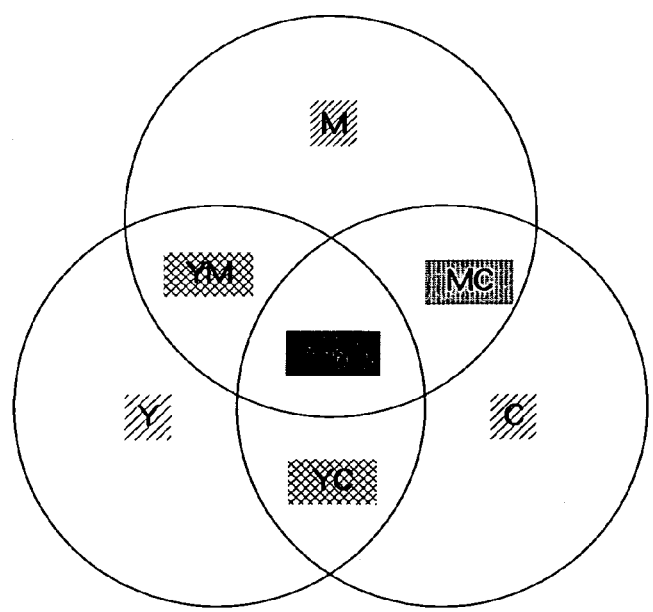

Generally, printed colors are made with a number of tiny ink dots of primary colors Y, M, C and K. Dots of each primary color have the specific size and number depending on the color represented. As shown in FIG. 12(a), Y, M and C inks having the specific wavelength-dependent transmittances give considerable influence to the relative spectral intensity of the illumination light reaching the paper substrate, while K (black) ink has the spectrally constant transmittance and give no influence. Neglecting K ink, printed surface consists of areas of Y, M and C inks and the superposition of those YM, MC, CA and YMC and unprinted area as shown in FIG. 12(b). As the result, fluorescence from printed paper depends on the dot area of each of inks and the superposition of those and the spectral transmittance of those namely the color represented.

Figure 2A:
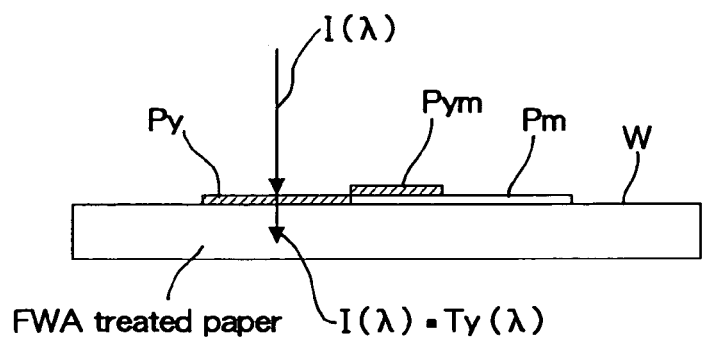
FIG. 2 explains the structure of printed layers of Y and M inks and the superposition of those on the fluorescent paper.
Figure 2B:
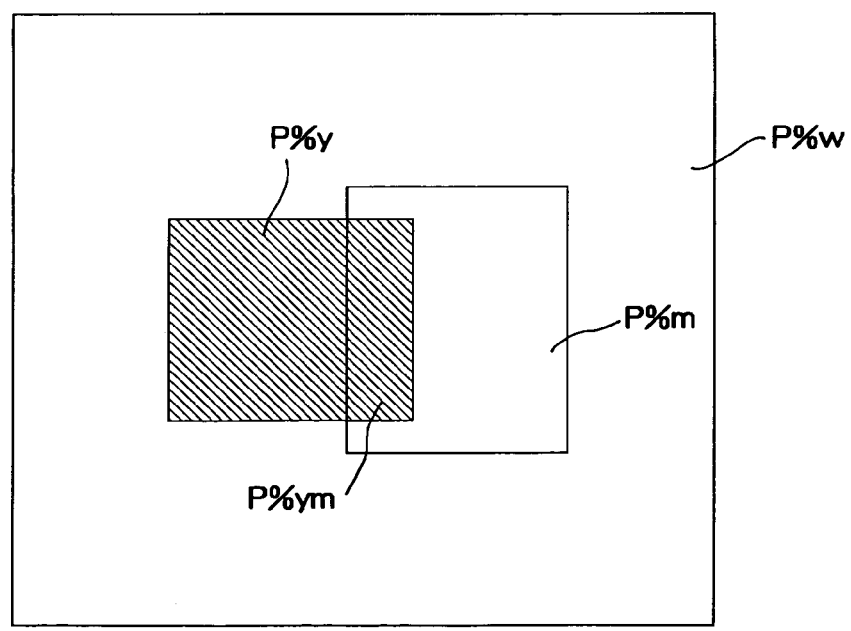

FIG. 2 schematically explains the structure of inks and the superposition of those and the influence to the incident light for the case of Y and M inks.

When the paper printed with Y and M inks of spectral transmittances $Ty(\lambda)$ and $Tm(\lambda)$ respectively is illuminated by the illumination of the spectral intensity $I(\lambda)$, while the unprinted area W receives the illumination intensity $I(\lambda)$ as it is, the areas printed with Y, M and the superposition of those Py, Pm and Pym receive the illumination intensies $I(\lambda)\cdot Ty(\lambda)$, $I(\lambda)\cdot Tm(\lambda)$, and $I(\lambda)\cdot Ty(\lambda)\cdot Tm(\lambda)$ respectively.

Accordingly, the effective spectral intensity $Ie(\lambda)$ is given by the sum of the abovementioned $I(\lambda)\cdot Ty(\lambda)$, $I(\lambda)\cdot Tm(\lambda)$, $I(\lambda)\cdot Ty(\lambda)\cdot Tm(\lambda)$, and $I(\lambda)$ weighted by the dot areas P % y, P % m, P % ym, and P % w=1–(P % y+P % m+P % ym) of those respectively as shown by Equation (30).

$$Ie(\lambda)=P\%\,y\cdot I(\lambda)\cdot Ty(\lambda)+P\%\,m\cdot I(\lambda)\cdot Tm(\lambda)+P\%\,ym\cdot I(\lambda)\cdot Ty(\lambda)\cdot Tm(\lambda)+P\%\,w\cdot I(\lambda) \qquad (30)$$

The fluorescent spectral radiance factor $F(\lambda)$ excited by the illumination of the effective spectral intensity $Ie(\lambda)$ is given by Equation (31) based on Equation (2).

$$F(\lambda)=\int F(\mu,\lambda)\cdot Ie(\mu)d\mu/I(\lambda)=\int F(\mu,\lambda)\cdot I(\mu)\cdot(P\%\,y\cdot Ty(\mu)+P\%\,m\cdot Tm(\mu)+P\%\,ym\cdot Ty(\mu)\cdot Tm(\mu)+P\%\,w)d\mu/I(\lambda) \qquad (31)$$

By introducing the effective bi-spectral luminescent radiance factor $Fe(\mu,\lambda)=(P\%\,y\cdot Ty(\mu)+P\%\,m\cdot Tm(\mu)+P\%\,c\cdot Tc(\mu)+P\%\,ym\cdot Ty(\mu)\cdot Tm(\lambda)+P\%\,w)\cdot F(\mu,\lambda)$, Equation (31) is rewritten by Equation (32)

$$F(\lambda)=\int Fe(\mu,\lambda)\cdot I(\mu)d\mu/I(\lambda) \qquad (32)$$

The above-explained principle can be expanded from the two ink (Y and M) system to the four ink (Y, M, C and K) system. Dot areas of four inks and the superposition of those (indicated by y, m, c, ym, mc, ca, ymc, and k, hereinafter) P % y, P % m, P % c, P % ym, P % mc, P % cy, P % ymc and P % k are obtained from the total spectral radiance factor measured by the illumination I1 of the incandescent lamps by a known method.

The dot area data obtained from the total spectral radiance factor by the incandescent lamp illumination of the negligible UV intensity are free from errors due to fluorescence. For calculating dot areas, the total spectral radiance factors $Bw1(\lambda)$, $By1(\lambda)$, $Bm1(\lambda)$, $Bc1(\lambda)$, $Bym1(\lambda)$, $Bmc1(\lambda)$, $Bcy1(\lambda)$, and $Bymc1(\lambda)$ of the unprinted area and the areas printed by four inks and the superposition of those with 100% dot area are measured and stored in BLRF storage 73 as the base data.

The effective bi-spectral luminescent radiance factor $Fe(\mu,\lambda)$ of the measuring area is estimated by Equation (33) using the dot area data P % y, P % m, P % c, P % ym, P % mc, P % cy, P % ymc, P % k, and P % w=1−ΣP %, where ΣP % is the sum of dot areas of all printed areas obtained by a known method, bi-spectral luminescent radiance factor $F(\mu,\lambda)$ of the paper stored in BLRF storage 73 in advance, and the spectral transmittances of those $Ty(\lambda)$, $Tm(\lambda)$, and $Tc(\lambda)$ also stored in BLRF storage 73 in advance.

$$Fe(\mu,\lambda)=(P\%\,y\cdot Ty(\mu)+P\%\,m\cdot Tm(\mu)+P\%\,c\cdot Tc(\mu)+P\%\,ym\cdot Ty(\mu)\cdot Tm(\lambda)+P\%\,mc\cdot Tm(\lambda)\cdot Tc(\mu)+P\%\,cy\cdot Tc(\lambda)\cdot Ty(\mu)+P\%\,ymc\cdot Ty(\mu)\cdot Tm(\lambda)\cdot Tc(\lambda)+P\%\,mc\cdot Tm(\lambda)\cdot Tc(\mu)+P\%\,w)\cdot F(\mu,\lambda) \qquad (33)$$

This procedure is not required for K ink having the spectrally constant transmittance.

The spectral transmittances of the superposition of Y, M and C inks are given as the products of spectral transmittances $Ty(\lambda)$, $Tm(\lambda)$, and $Tc(\lambda)$ of Y, M, and C inks.

The total spectral radiance factor of the measuring area illuminated by a specified test illumination is calculated with the estimated effective bi-spectral luminescent radiance factor $Fe(\mu,\lambda)$ by the same procedure as in the case of (A) mentioned before.

The effective bi-spectral luminescent radiance factor $Fe(\mu,\lambda)$ can be alternatively estimated by Equation (34) using dot area data of inks and the superposition of those and the bi-spectral luminescent radiance factors of unprinted area and areas printed by four inks and the superposition of those with 100% dot area $F(\mu,\lambda)$, $Fy(\mu,\lambda)$, $Fm(\mu,\lambda)$, $Fc(\mu,\lambda)$, $Fym(\mu,\lambda)$, $Fmc(\mu,\lambda)$, $Fcy(\mu,\lambda)$, and $Fymc(\mu,\lambda)$.

$$Fe(\mu,\lambda)=(P\%\,y\cdot Fy(\mu,\lambda)+P\%\,m\cdot Fm(\mu,\lambda)+P\%\,c\cdot Fc(\mu,\lambda)+P\%\,m\cdot Fym(\mu,\lambda)+P\%\,mc\cdot Fmc(\mu,\lambda)+P\%\,ymc\cdot Fymc(\mu,\lambda)+P\%\,w\cdot F(\mu,\lambda) \quad (34)$$

The principle of the measuring method of the total spectral radiance factor of a printed surface on paper treated by FWA (referred to as "printed fluorescent sample" hereinafter) mentioned above can be summarized as below.

B1. The effective bi-spectral luminescent radiance factor of the printed surface on paper treated by FWA is estimated from the bi-spectral luminescent radiance factor of the paper and the dot areas and spectral transmittances of the inks and the superposition of those.

B2. A1 through A4 in the summarization of the method for measuring the total spectral radiance factor of a fluorescent sample is performed with the effective bi-spectral luminescent radiance factor.

B3. Dot areas are obtained from the total spectral radiance factor measured by the illumination having negligible UV intensity.

<Procedures for Measuring the Total Spectral Radiance Factor of a Printed Surface on Paper Treated by FWA>

Figure 5:
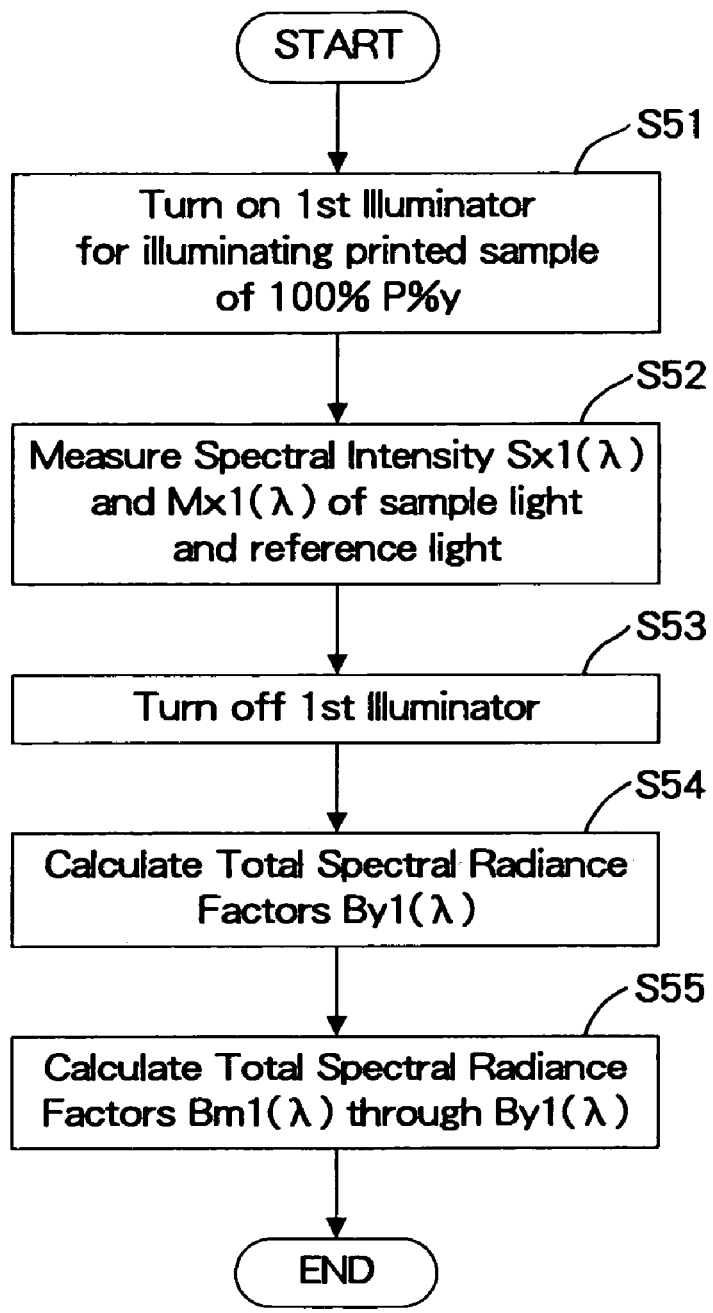
FIG. 5 shows a flowchart for measuring standard prints for the measuring method of the present invention.

Procedures for measuring a total spectral radiance factor $Bxs(\lambda)$ of a printed surface on FWA-treated paper by measuring apparatus 10 comprises the procedure for measuring the standard prints performed in advance and the procedure for sample measurement performed thereafter. FIG. 5 exemplarily shows a flowchart for measuring standard prints. As shown there, after the white calibration performed, controller 7 turns on first illuminator 2 (incandescent lamps 21) to illuminate the surface printed by Y ink with 100% dot area (P % y) by the illumination light LA (illumination light I1) (Step S51). Then, the spectral intensity $Sx1(\lambda)$ of the sample light by said illumination LA is measured by dual channel spectral unit 6. Simultaneously, the spectral intensity $Mx1(\lambda)$ of the illumination light LA is measured and the spectral intensity data $Sx1(\lambda)$ and $Mx1(\lambda)$ are stored in spectral intensity storage 71 (Step S52). Then, controller 7 turns off first illuminator 2 (Step S53).

Then, controller 7 calculates the-total radiance factor $By1(\lambda)$ of the surface printed with Y ink of 100% dot area (standard print for Y) under the illumination LA by Equation (35) corresponding to Equation (24) using $Sx1(\lambda)$ and $Mx1(\lambda)$ stored in step S52 and stores $By1(\lambda)$ in dot area storage 75 (Step S54).

$$By1(\lambda)=C1(\lambda)\cdot Sx1(\lambda)/Mx1(\lambda) \quad (35)$$

Similarly, the above-mentioned steps S51 through S55 are repeated to the standard prints printed with 100% of P % m, P % c, P % ym, P % mc, P % cy, P % ymc, and P % k and the unprinted paper and $Bm1(\lambda)$, $Bc1(\lambda)$, $Bym1(\lambda)$, $Bmc1(\lambda)$, $Bymc1(\lambda)$, $Bk1(\lambda)$, and $Bw1(\lambda)$ are respectively calculated and stored in dot area storage 75 (Step S55).

Figure 6:
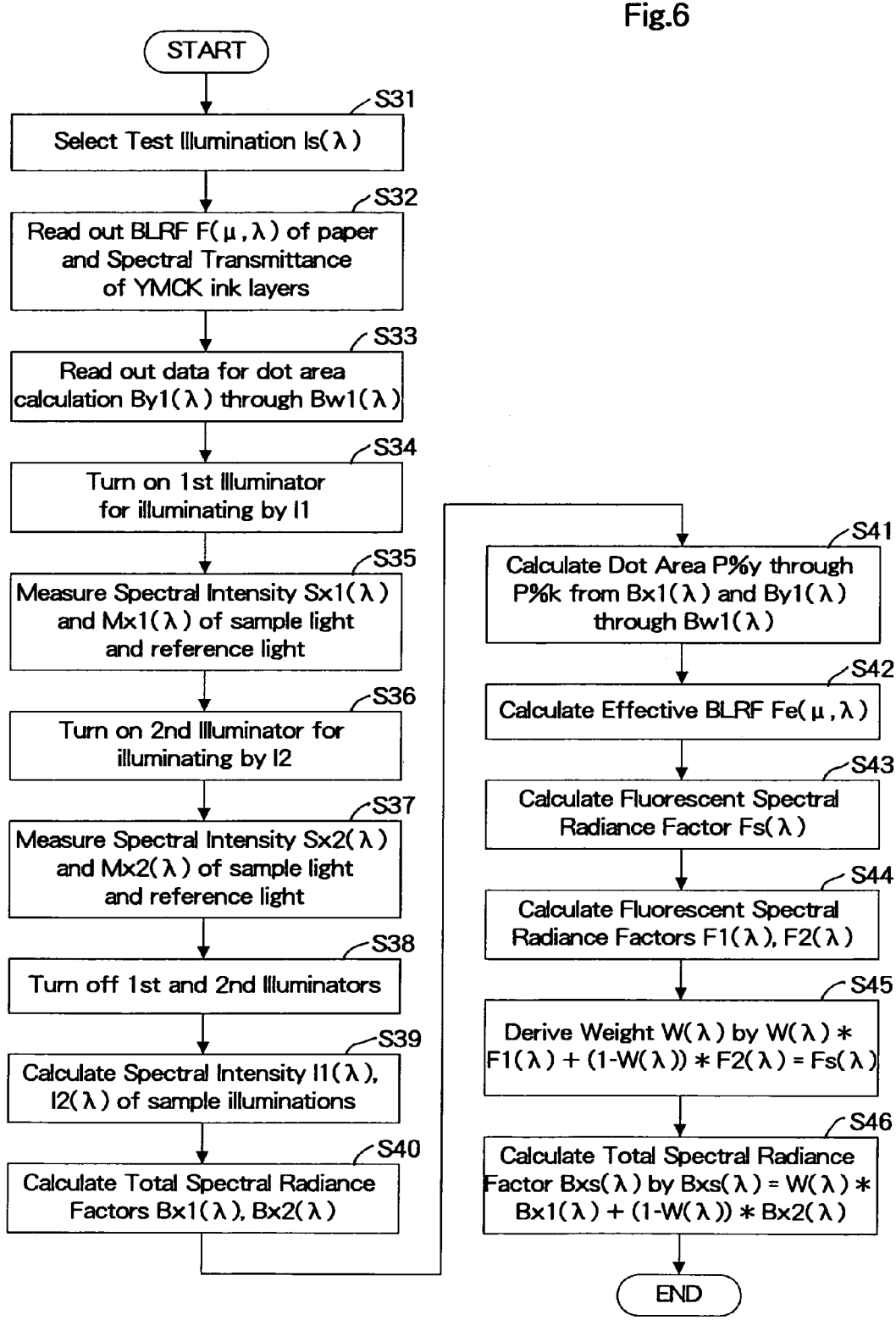
FIG. 6 shows a flowchart for measuring a total spectral radiance factor of a printed surface on a fluorescent paper by the measuring method of the present invention.

FIG. 6 exemplarily shows the flowchart for measuring a printed surface on paper treated by FWA. First, the test illumination Is is selected. That is controller 7 reads out the spectral intensity data $Is(\lambda)=Is(\mu)$ of the selected test illumination from test illumination storage 72 (Step S31). Next, the type of paper for print and that of the ink set (YMC inks) are selected. That is, controller 7 reads out the bi-spectral fluorescent radiance factor data $F(\mu,\lambda)$ close to that of the paper and the spectral transmittances $Ty(\lambda)$, $Tm(\lambda)$, and $Tc(\lambda)$ of the ink layers printed with the selected inks from BLRF storage 73 (Step S32). Then, controller 7 reads out the total spectral radiance factor $Bm1(\lambda)$, $Bc1(\lambda)$, $Bym1(\lambda)$, $Bmc1(\lambda)$, $Bymc1(\lambda)$, $Bk1(\lambda)$, and $Bw1(\lambda)$ measured by illuminating the standard prints printed with 100% of P % m, P % c, P % ym, P % mc, P % cy, P % ymc, and P % k and unprinted paper by first illuminator 2 and stored in dot area storage 75 in step S55 (Step S33).

Next, controller 7 turns on first illuminator 2 (incandescent lamps 21) to illuminate the printed surface on FWA-treated paper and the spectral intensity $Sx1(\lambda)$ of the sample light by said illumination light LA is measured by dual channel spectral unit 6 (spectral measurement means). Simultaneously, the spectral intensity $Mx1(\lambda)$ of the illumination light LA is measured and the spectral intensity data $Sx1(\lambda)$ and $Mx1(\lambda)$ are stored in spectral intensity storage 71 (Step S35). After that, controller 7 turns on the second illuminator 3 (UV LED's 31) keeping first illuminator 2 on to illuminate the sample by illumination light LB (illumination light I2) by both first and second illuminators (Step S36), and the spectral intensity $Sx2(\lambda)$ of the sample light by the illumination light LB is measured. Simultaneously, the spectral intensity $Mx2(\lambda)$ of the illumination light LB is measured and the spectral intensity data $Sx2(\lambda)$ and $Mx2(\lambda)$ are stored in spectral intensity storage 71 (Step S37). Then, both first and second illuminators are turned off (Step S38).

Then, controller 7 converts the spectral-intensities $Mx1(\lambda)$ and $Mx2(\lambda)$ of the reference light to the spectral intensities $I1(\lambda)$ and $I2(\lambda)$ of the sample illuminations (LA and LB) by Equations (19) and (20) and stores in spectral intensity storage 71 (Step S39). And, controller 7 calculates the total radiance factors $Bx1(\lambda)$ and $Bx2(\lambda)$ under the illuminations LA and LB (I1 and I2) by Equation (23) and (24) using $Sx1(\lambda)$, $Sx2(\lambda)$, $Mx1(\lambda)$, and $Mx2(\lambda)$ stored in steps S35 and S37 (Step S40).

Then, controller 7 calculates the dot areas P % m, P % c, P % ym, P % mc, P % cy, P % ymc and P % k of the YMCK inks and the superposition of those of the printed fluorescent sample from $Bx1(\lambda)$ obtained in step S40 and $Bm1(\lambda)$, $Bc1(\lambda)$, $Bym1(\lambda)$, $Bmc1(\lambda)$, $Bymc1(\lambda)$, $Bk1(\lambda)$, and $Bw1(\lambda)$ read out in step S33 (Step S41) and calculates the effective bi-spectral luminescent radiance factor $Fe(\mu,\lambda)$ based on the dot areas P % m, P % c, P % ym, P % mc, P % cy, P % ymc, and P % k, the bi-spectral luminescent radiance factor data $F(\mu,\lambda)$, and the spectral transmittances $Ty(\lambda)$, $Tm(\lambda)$, and $Tc(\lambda)$ of the YMC inks read out in step S32 (Step S42). Next, controller 7 calculates the fluorescent spectral radiance factor $Fs(\lambda)$ of the sample under the selected test illumination by Equation (36) using the spectral intensity data $Is(\lambda)=Is(\mu)$ and the calculated effective bi-spectral luminescent radiance factor data $Fe(\mu,\lambda)$ (Step S43).

$$Fs(\lambda)=Fe(\mu,\lambda)\cdot Is(\mu)d\mu/Is(\lambda) \quad (36)$$

Next, controller 7 calculates the fluorescent radiance factors $F1(\lambda)$ and $F2(\lambda)$ under the illumination LA and LB (I1 and I2) by Equations (37) and (38) using $I1(\lambda)$ and $I2(\lambda)$ obtained in step S39 and the calculated effective bi-spectral luminescent radiance factor data Fe($\mu,\lambda$) (Step S44).

$$F1(\lambda)=\int Fe(\mu,\lambda)\cdot I1(\mu)d\mu/I1(\lambda) \qquad (37)$$

$$F2(\lambda)=\int Fe(\mu,\lambda)\cdot I2(\mu)d\mu/I2(\lambda) \qquad (38)$$

Next, controller 7 determines the weight W($\lambda$) for each wavelength by solving Equation (39) including the fluorescent radiance factors F1($\lambda$) and F2($\lambda$) calculated above and Fs($\lambda$) calculated in step S43 (Step S45).

$$W(\lambda)\cdot F1(\lambda)+(1-W(\lambda))\cdot F2(\lambda)=Fs(\lambda) \qquad (39)$$

And controller 7 calculates the total spectral radiance factor Bxs($\lambda$) of the sample under the test illumination by Equation (40) using Bx1($\lambda$) and Bx2($\lambda$) calculated in step S40 and the weight W($\lambda$) obtained in step S34 (Step S46).

$$Bxs(\lambda)=W(\lambda)\cdot Bx1(\lambda)+(1-W(\lambda))\cdot Bx2(\lambda) \qquad (40)$$

As mentioned above, the optical property that is the total spectral radiance factor of a fluorescent sample including a printed fluorescent sample under a specified test illumination is measured by the method of this embodiment or by the measuring apparatus applying said method. Advantages of said method and measuring apparatus can be summarized as below.

By knowing the bi-spectral luminescent radiance factor which is close to that of the sample, the data replaces an actual fluorescence standard and as the result;

C1. Errors due to the aging of the fluorescent standard are replaced by much small errors due to the aging of the spectral measurement means for the reference light.

C2. There is no error due to differences among fluorescent standards.

C3. Frequent renewals of the fluorescent standard are not required and the cost and time for that is eliminated.

C4. A UV correction prior to the sample measurement is not required.

C5. As the virtual illumination is synthesized based on the spectral intensities of the illuminations at each time of sample measurement, no error due to fluctuations of the illuminations is introduced.

C6. More than one bi-spectral luminescent radiance factors or bi-spectral radiance factors and spectral intensities of more than one test illuminations can be stored in advance and those suitable for the sample to be measured and the purpose of the measurement can be selected prior to sample measurement.

C7. The bi-spectral luminescent radiance factor data or the bi-spectral radiance factor data and the test illumination data can be added or renewed via internet (web).

C8. The total spectral luminescent radiance factor of a printed surface on paper treated by FWA is measurable and the printed colors can be evaluated taking the influence of fluorescence in account.

C9. Printed colors by a printer or the like can be evaluated taking the influence of fluorescence in account without any additional operation but storing the aforementioned data of the paper and the inks used by the printer or the like in advance.

As mentioned above, the method of this embodiment enables to obtain the total spectral radiance factor Bxs($\lambda$) of a fluorescent sample virtually illuminated by a specified test illumination Is by performing process 1 through 4 described below from a bi-spectral luminescent radiance factor F($\mu,\lambda$) or a bi-spectral radiance factor B($\mu,\lambda$) which is close to the bi-spectral luminescent radiance factor or the bi-spectral radiance factor of the sample, the spectral intensity Is($\lambda$) of the test illumination Is, the measured spectral intensities I1($\lambda$) and I2($\lambda$) of first and second actual illuminations (illumination LA and LB) which are different from each other, and the measured spectral intensities Sx1($\lambda$) and Sx2($\lambda$) of the light emitted from the sample illuminated by said first and second illuminations I1 and I2.

Process 1 for calculating the fluorescent spectral radiance factor Fs($\lambda$) or the total spectral radiance factor Bs($\lambda$) by said illumination for testing Is from said bi-spectral luminescent radiance factor F($\mu,\lambda$) or bi-spectral radiance factor B($\mu,\lambda$) and the spectral intensity Is($\lambda$) of said illumination for testing.

Process 2 for determining a weight W($\lambda$) at each wavelength so that the fluorescent spectral radiance factor Fc($\lambda$) or the total spectral radiance factor Bc($\lambda$) by the spectral intensity Ic($\lambda$)=W($\lambda$)·I1($\lambda$)+(1−W($\lambda$))·I2($\lambda$) of the illumination Ic synthesized by linear combination of said first and second actual illuminations weighted by said weight W($\lambda$) matches said fluorescent spectral radiance factor Fs($\lambda$) or total spectral radiance factor Bs($\lambda$) by said test illumination Is.

Process 3 for calculating the spectral intensity Sxc($\lambda$)=W($\lambda$)·Sx1($\lambda$)+(1−W($\lambda$))·Sx2($\lambda$) of the light emitted from the sample virtually illuminated by said synthesized illumination Ic by linear combination of said measured spectral intensities Sx1($\lambda$) and Sx2($\lambda$) weighted by said weight W($\lambda$). Process 4 for calculating the total spectral radiance factor Bxs($\lambda$) of the sample illuminated by said test illumination Is from the spectral intensity Ic($\lambda$) of said synthesized illumination Ic and said spectral intensity Sxc($\lambda$) of the light emitted from sample illuminated by said synthesized illumination Ic.

This method of the embodiment requires no fluorescent standard and no UV correction using it required in conventional methods. As the result, errors due to the renewal of the fluorescent standard and the aging before the renewal are eliminated. Further, since the weight W($\lambda$) is determined based on the spectral intensities of the actual illuminations measured at each time of sample measurement, no error due to fluctuations of the illumination is introduced, and accordingly an optical property (total spectral radiance factor) of a fluorescent sample illuminated by a specified test illumination is obtained accurately. Reference values of conventional fluorescent standards are derived from the bi-spectral luminescent radiance factor F($\mu,\lambda$) or the bi-spectral radiance factor B($\mu,\lambda$) measured by a standardizing laboratories (NRC in Canada for example), and by using said bi-spectral luminescent radiance factor data or bi-spectral radiance-factor data, the method of the present invention can be introduced maintaining the compatibility to the conventional method.

As mentioned above, the total spectral radiance factor Bxs($\lambda$) of a fluorescent sample virtually illuminated by a specified test illumination Is is obtained by performing process 1 through 4 described below from a bi-spectral luminescent radiance factor F($\mu,\lambda$) or a bi-spectral radiance factor B($\mu,\lambda$) which is close to the bi-spectral luminescent radiance factor or the bi-spectral radiance factor of the sample, the spectral intensity Is($\lambda$) of said test illumination Is, measured intensities I1($\lambda$) and I2($\lambda$) of first and second actual illuminations I1 and I2 which are different from each other, and the measured total spectral radiance factor Bx1($\lambda$) and Bx2($\lambda$) of the sample illuminated by said first and second illuminations I1 and I2.

Process 1 for calculating the fluorescent spectral radiance factor Fs($\lambda$) or the total spectral radiance factor Bs($\lambda$) by said illumination for testing Is from said bi-spectral luminescent radiance factor F($\mu,\lambda$) or bi-spectral radiance factor B($\mu,\lambda$) and the spectral intensity Is($\lambda$) of said illumination for testing.

Process 2 for calculating the fluorescent spectral radiance factors F1($\lambda$) and F2($\lambda$) or the total spectral radiance factors $B1(\lambda)$ and $B2(\lambda)$ by said first and second illuminations I1 and I2 from said bi-spectral luminescent radiance factor $F(\mu,\lambda)$ or bi-spectral radiance factor $B(\mu,\lambda)$ and said measured spectral intensities $I1(\lambda)$ and $I2(\lambda)$ of said first and second illuminations I1 and I2.

Process 3 for determining a weight $W(\lambda)$ at each wavelength so that the fluorescent spectral radiance factor $Fc(\lambda) = W(\lambda) \cdot F1(\lambda) + (1-W(\lambda)) \cdot F2(\lambda)$ or the total spectral radiance factor $Bc(\lambda) = W(\lambda) \cdot B1(\lambda) + (1-W(\lambda)) \cdot B2(\lambda)$ synthesized by linear combination of said fluorescent spectral radiance factors $F1(\lambda)$ and $F2(\lambda)$ or total spectral radiance factors $B1(\lambda)$ and $B2(\lambda)$ weighted by said weight $W(\lambda)$, matches said fluorescent spectral radiance factor $Fs(\lambda)$ or total spectral radiance factor $Bs(\lambda)$ by said illumination for testing Is.

Process 4 for calculating the total spectral radiance factor $Bxs(\lambda) = W(\lambda) \cdot Bx1(\lambda) + (1-W(\lambda)) \cdot Bx2(\lambda)$ of the sample illuminated by said illumination for testing Is from said measured total spectral radiance factors $Bx1(\lambda)$ and $Bx2(\lambda)$ of the sample and said weight $W(\lambda)$.

This method of the embodiment requires no fluorescent standard and no UV correction using it required in conventional methods. As the result, errors due to the renewal of fluorescent standard and the aging before the renewal are eliminated. Further, since the weight $W(\lambda)$ is determined based on the spectral intensities of the actual illuminations-measured at each time of measurement, no error due to fluctuations of the illumination is introduced. Further, the processing is simplified since the total spectral radiance factor $Bxs(\lambda)$ of the sample virtually illuminated by the specified illumination for testing Is is obtained by linear combination of said measured total spectral radiance factors $Bx1(\lambda)$ and $Bx2(\lambda)$ of the sample illuminated by first and second actual illuminations I1 and I2 weighted by said weight $W(\lambda)$. Here, for calculating the total spectral radiance factor $B1(\lambda)$ and $B2(\lambda)$ and $Bx1(\lambda)$ and $Bx2(\lambda)$, both first and second illuminations need to have the intensity at every wavelengths $\lambda$ ($I1(\lambda) > 0$ and $I2(\lambda) > 0$).

For the measurement of a sample consisting of a substrate treated by FWA (hereinafter referred to as "fluorescent substrate") and more than one colorants P1 through Pm (YMCK inks for example), the effective bi-spectral luminescent radiance factor $Fe(\mu,\lambda)$ or the effective bi-spectral radiance factor $Be(\mu,\lambda)$ of said sample is calculated prior to aforementioned process 1 through 4 based on a bi-spectral luminescent radiance factor $F(\mu,\lambda)$ or a bi-spectral radiance factor $B(\mu,\lambda)$ which is close to the bi-spectral luminescent radiance factor or the bi-spectral radiance factor of said substrate, spectral transmittances $T1(\lambda)$ through $Tm(\lambda)$ (corresponding to $Ty(\lambda)$, $Tm(\lambda)$ and $Tm(\lambda)$) of said colorants P1 through Pm or spectral transmittances $T1(\lambda)$ through $Tn(\lambda)$ (corresponding to $Ty(\lambda)$ through $Tymc(\lambda)$) of said colorants P1 through Pm and the superposition of those Pm+1 through Pn ($n \geq m$), and dot areas P%1 through P%n of said colorants and the superposition of those in the measuring area. Using said effective bi-spectral luminescent radiance factor $Fe(\mu,\lambda)$ or effective bi-spectral radiance factor $Be(\mu,\lambda)$, the optical property of the colored fluorescent substrate is obtained by the method of the present invention. As the result, printed colors on a fluorescent substrate such as paper treated by FWA can be accurately measured without any cost and time for maintaining a fluorescent standard and for a UV correction using it.

For the measurement of a sample consisting of a substrate treated by FWA and more than one colorants P1 through Pm, the effective bi-spectral luminescent radiance factor $Fe(\mu,\lambda)$ or the effective bi-spectral radiance factor $Be(\mu,\lambda)$ of said sample is calculated prior to the aforementioned process 1 through 4 based on bi-spectral luminescent radiance factors $F(\mu,\lambda)$ and $F1(\mu,\lambda)$ through $Fn(\mu,\lambda)$ or bi-spectral radiance factors $B(\mu,\lambda)$ and $B1(\mu,\lambda)$ through $Bn(\mu,\lambda)$ which are close to the bi-spectral luminescent radiance factors or the bi-spectral radiance factors of said substrate and the substrates colored by aforementioned colorants and the superposition of those and dot areas P%1 through P%n of said colorants and the superposition of those in the measuring area. Using said effective bi-spectral luminescent radiance factor $Fe(\mu,\lambda)$ or effective bi-spectral radiance factor $Be(\mu,\lambda)$, the optical property of the colored fluorescent substrate is obtained by the method of the present invention. As the result, printed colors on a fluorescent substrate such as paper treated by FWA can be accurately measured without any cost and time for maintaining a fluorescent standard and for a UV correction using it.

Since the dot areas P1% through Pn % of the colorants and the superposition of those are calculated from at least either of the measured total spectral radiance factor $Bx1(\lambda)$ or the $Bx2(\lambda)$ of the sample illuminated by the actual illumination I1 or I2, the total spectral radiance factor of the sample virtually illuminated by the illumination for testing can be measured without any bothersome task for inputting the dot area data of the sample.

As the total spectral radiance factor from which dot areas of the colorants and the superposition of those are calculated is measured by the illumination having low relative intensity in UV region, obtained dot areas are free from errors due to fluorescence of the substrate, and accordingly the total spectral radiance factor of a printed fluorescent sample illuminated by an specified illumination for testing can be accurately measured.

In a measuring apparatus of this embodiment, the sample is illuminated by first and second actual illuminations I1 and I2 (illumination light LA and LB) by a first and a second illuminators 2 and 3 whose spectral intensities are different from each other, and the spectral intensity of the light emitted from the sample is measured by the first channel of dual channel spectral unit 6 for sample light and the spectral intensities of said illumination light I1 and I2 are measured by the second channel of dual channel spectral unit 6 for illumination light. A bi-spectral luminescent radiance factor $F(\mu,\lambda)$ or a bi-spectral radiance factor $B(\mu,\lambda)$ which is close to the bi-spectral luminescent radiance factor or the bi-spectral radiance factor of the sample and the spectral intensity of a light for testing is stored in the storages 72 and 73. A controller 7 consecutively turns on said first and second illuminations 2 and 3, calculates the spectral intensities $Sx1(\lambda)$ and $Sx2(\lambda)$ of the light emitted from the sample or the total spectral radiance factors $Bx1(\lambda)$ and $Bx2(\lambda)$ of the sample illuminated by said first and second actual illuminations I1 and I2 and the spectral intensities $I1(\lambda)$ and $I2(\lambda)$ of said first and second illuminations I1 and I2 from the data measured by said spectral unit 6, and calculates the total spectral radiance factor $Bxs(\lambda)$ of the sample virtually illuminated by said illumination for testing Is. As the result, no fluorescent standard and no bothersome UV correction using it required in conventional methods are required, and accordingly, the procedure of measurement is simplified and the efficiency is improved. Further, errors due to the renewal of the fluorescent standard and to the aging before the renewal are eliminated. Thus, an optical property (total spectral radiance factor) of a fluorescent sample illuminated by a specified illumination for testing can be obtained accurately.

Reference values of conventional fluorescent standards are derived from the bi-spectral luminescent radiance factor $F(\mu,\lambda)$ or the bi-spectral radiance factor $B(\mu,\lambda)$ measured by a standardizing laboratories (NRC in Canada for example), and by using said bi-spectral luminescent radiance factor data or bi-spectral radiance factor data, the method of this embodiment can be introduced maintaining the compatibility to the conventional method. And, more than one bi-spectral luminescent radiance factors or bi-spectral radiance factors and spectral intensities of more than one illuminations for testing can be stored in the apparatus in advance, and those suitable for the sample to be measured and the purpose of the measurement can be selected prior to measurement. These data can be stored in the factory before the TV correction with it and added or renewed via internet (web) after shipment.

By further storing a bi-spectral luminescent radiance factor $F(\mu,\lambda)$ or a bi-spectral radiance factor $B(\mu,\lambda)$ which is close to the bi-spectral luminescent radiance factor or the bi-spectral radiance factor of a fluorescent substrate, spectral transmittances $T1(\lambda)$ through $Tm(\lambda)$ (corresponding to $Ty(\lambda)$, $Tm(\lambda)$ and $Tm(\lambda)$) of colorants P1 through Pm applied on said fluorescent substrate or spectral transmittances $T1(\lambda)$ through $Tn(\lambda)$ (corresponding to $Ty(\lambda)$ through $Tymc(\lambda)$) of said colorants P1 through Pm and the superposition of those Pm+1 through Pn ($n \geq m$), and dot areas P %1 through P % n of the colorants and the superposition of those in the measuring area, the total spectral radiance factor $Bxs(\lambda)$ of the sample virtually illuminated by the specified illumination for testing Is is calculated based on said data further stored. Thus, printed colors on a fluorescent substrate can be measured accurately without any cost and time for maintaining a fluorescent standard and for a UV correction using it. Here, dot area data can be input as numerical data or measured by a known method.

Data of more than one bi-spectral luminescent radiance factors or bi-spectral radiance factors, spectral transmittances of more than one sets of inks, and spectral intensities of more than one illuminations for testing can be stored in the apparatus as the base data in advance, and those suitable for the sample to be measured and the purpose of the measurement can be selected prior to measurement. These data can be stored in the factory before shipment and added or renewed via internet (web) after shipment.

By further storing bi-spectral luminescent radiance factors $F(\mu,\lambda)$ and $F1(\mu,\lambda)$ through $Fn(\mu,\lambda)$ or bi-spectral radiance factors $B(\mu,\lambda)$ and $B1(\mu,\lambda)$ through $Bn(\mu,\lambda)$ which are close to the bi-spectral luminescent radiance factors or the bi-spectral radiance factors of a fluorescent substrate and the substrates colored by colorants P1 through Pm and the superposition of those Pm+1 through Pn ($n \geq m$) and the dot areas P %1 through P % n of the colorants and the superposition of those in the measuring area, the total spectral radiance factor $Bxs(\lambda)$ of the sample virtually illuminated by the specified illumination for testing Is is calculated base on said data further stored. Thus, printed colors on the fluorescent substrate can be measured accurately without any cost and time for maintaining a fluorescent standard and for a UV correction using it. Here, dot area data can be input as numerical data or measured by a known method.

Bi-spectral luminescent radiance factor data or bi-spectral radiance factor data for more than one aforementioned combinations, each of which is a combinations of a fluorescent substrate and a set of colorants, and spectral intensities of more than one test illuminations can be stored in the apparatus as the base data in advance, and those suitable for the sample to be measured and the purpose of the measurement can be selected prior to measurement. These data can be stored in the factory before shipment and added or renewed via internet (web) after shipment.

Since the dot areas P1% through Pn % of the colorants and the superposition of those are calculated from at least either of the measured total spectral radiance factor $Bx1(\lambda)$ or $Bx2(\lambda)$ of the sample illuminated by the actual illumination I1 or I2, the total spectral radiance factor of the sample virtually illuminated by the specified illumination for testing can be measured without bothersome task to input the dot area data of the sample.

As the total spectral radiance factor from which dot areas of the colorants and the superposition of those is calculated is measured by the illumination having low relative intensity in UV region, the obtained dot areas are free from errors due to the fluorescence of the substrate, and accordingly the total spectral radiance factor of the sample virtually illuminated by the illumination for testing can be accurately measured.

Since the first illuminator comprises incandescent lamps and the second illuminator comprises UV LED's, both illuminations with relatively sufficient and low UV intensities can be easily realized with low cost and simple structure without any filter.

Since the first illumination (illumination light LA) is provided by the first illuminator (incandescent lamps) and the second illumination (illumination light LB) is provided by both first and second illuminator (incandescent lamps and UV LED's), the illumination with sufficient relative UV intensity and the illumination with low relative UV intensity can be realized with low cost and simple structure without any filter. As both first and second illuminations have the intensity in visible region, the excitation efficiency of the illumination for fluorescence at each wavelength relative to the illumination intensity at the same wavelength can be calculated, and accordingly whole calculation procedure can be simplified.

Since both first and second illuminator have no intensity out of measurable wavelength region of the spectral measurement means for illumination light, the spectral intensities of said first and second illuminations in the wavelength region contributing to the excitation and fluorescence of FWA can be thoroughly measured, and accordingly the total spectral radiance factor can be obtained accurately.

The above-mentioned embodiment has additional embodiments as below.

(1) When introducing relative spectral integrated excitation efficiency $e(\lambda)=E(\lambda)/I(\lambda)$, where $E(\lambda)$ is the spectral integrated excitation efficiency of Equation 4 and $I(\lambda)$ is the illumination intensity at $\lambda$, the aforementioned virtual illumination Ic can be synthesized by combination of illumination light LA and LB so as to provide the same relative spectral integrated excitation efficiency as that of the specified test illumination. If it is accomplished, the total spectral radiance factor of the sample by the synthesized illumination is same as that by the test illumination. For synthesizing the virtual illumination mentioned above, the spectral integrated excitation efficiencies of the sample by the test illumination and the illumination light LA and LB need to be calculated, and for calculating the spectral integrated excitation efficiencies, the bi-spectral excitation efficiency $Q(\mu,\lambda)$ which is close to that of the sample is required. In aforementioned embodiment, the bi-spectral luminescent radiance factor $F(\mu,\lambda)$ or the bi-spectral radiance factor $B(\mu,\lambda)$ is used as the bi-spectral excitation efficiency $Q(\mu,\lambda)$ where the spectral integrated excitation efficiency $E(\lambda)=\int Q(\mu,\lambda),I(\mu)d\mu$ is replaced by the fluorescent spectral radiance factor $F(\lambda)=\int F(\mu,\lambda)\cdot I(\mu)d\mu$ or the total spectral radiance factor $B(\lambda)=\int B(\mu,\lambda)\cdot I(\mu)d\mu$. As the present invention doesn't requires information about the spectral-fluorescence intensity given by the bi-spectral luminescent radiance factor $F(\mu,\lambda)$ or the bi-spectral radiance factor $B(\mu,\lambda)$, the bi-spectral excitation efficiency $Q(\mu,\lambda)$ which doesn't give information about the spectral fluorescence intensity is sufficient. When the dependence of the excitation efficiency on the fluorescence wavelength is negligible, bi-spectral excitation efficiency $Q(\mu,\lambda)$ can be replaced by the spectral excitation efficiency $Q(\mu)$ and methods using the $Q(\mu)$ are included in the embodiment.

(2) Aforementioned embodiment comprises a first illuminator provided with incandescent lamps and a second illuminator provided with UV LED's and illuminates the sample by the illumination light LA by first illuminator and the second illumination light LB by both first and second illuminators. Alternatively, the illumination light LA and LB can be numerically produced from the spectral intensities $Sx'1(\lambda)$ and $Sx'2(\lambda)$ of the sample light and the spectral intensities $R'1(\lambda)$ and $R'2(\lambda)$ of the illumination light obtained by separately turning on first and second illuminators. That is, the spectral intensities $Sx1(\lambda)$ and $R1(\lambda)$ of the sample light and the illumination light for the illumination light LA is given by $Sx1(\lambda)=Sx'1(\lambda)$ and $R1(\lambda)=R'1(\lambda)$ respectively, and the spectral intensities $Sx2(\lambda)$ and $R2(\lambda)$ for the illumination light LB is given by $Sx2(\lambda)=Sx'1(\lambda)+Sx'2(\lambda)$ and $R2(\lambda)=R'1(\lambda)+R'2(\lambda)$ respectively.

(3) Aforementioned embodiment uses two different illuminations LA and LB. Differently, more than two different illuminations can be used. In this case, the weight is determined for each illumination (the sum of those equals to 1).

(4) Illumination light LA and LB can be produced by inserting either of two filters of different spectral transmission characteristics in the flux from a single light source.

(5) Printed colors by inks containing fluorescent material can be measured by applying Equation (34) of aforementioned embodiment for measuring printed color on fluorescent substrate described in (B). In this case, bi-spectral luminescent radiance factors $F(\mu,\lambda)$ or bi-spectral radiance factors $B(\mu,\lambda)$ which are close to those of surfaces printed by inks including said inks containing fluorescent material and the superposition of those are stored in advance.

(6) One or more test illuminations can be selected from the test illumination storage storing more than one test illuminations such as standard illuminants D65, D50, and C of daylight and illuminant F's of fluorescent lamp. In this case, controller 7 calculates and outputs the total spectral radiance factor or the colorimetric values derived therefrom of the sample for each of selected test illuminations.

(7) One of more than one bi-spectral luminescent radiance factors or bi-spectral radiance factors stored in BLRF storage 73 which are close to those of fluorescent products possibly measured can be selected. In this case, controller 7 calculates and outputs the total spectral radiance factors or the colorimetric values of the sample based on the selected bi-spectral luminescent radiance factor or the bi-spectral radiance factor. Similarly, for the measurement of printed colors on the fluorescent paper, (a) one of bi-spectral luminescent radiance factors or bi-spectral radiance factors for more than one types of paper and one of spectral transmittances of more than one types-of inks (YMCK inks for example) and the superposition of those stored in BLRF storage 73 can be selected or (b) one of more than one sets of bi-spectral luminescent radiance factors or bi-spectral radiance factors stored in BLRF storage 73, each of which is for a type of fluorescent paper and the fluorescent papers printed by a type of inks and the superposition of the inks, can be selected. Method (a) storing data for paper and data for inks independently requires less memory, while method (b) storing bi-spectral luminescent radiance factor or bi-spectral radiance factor data for all combinations of the selected paper and inks is more accurate.

Figure 7:
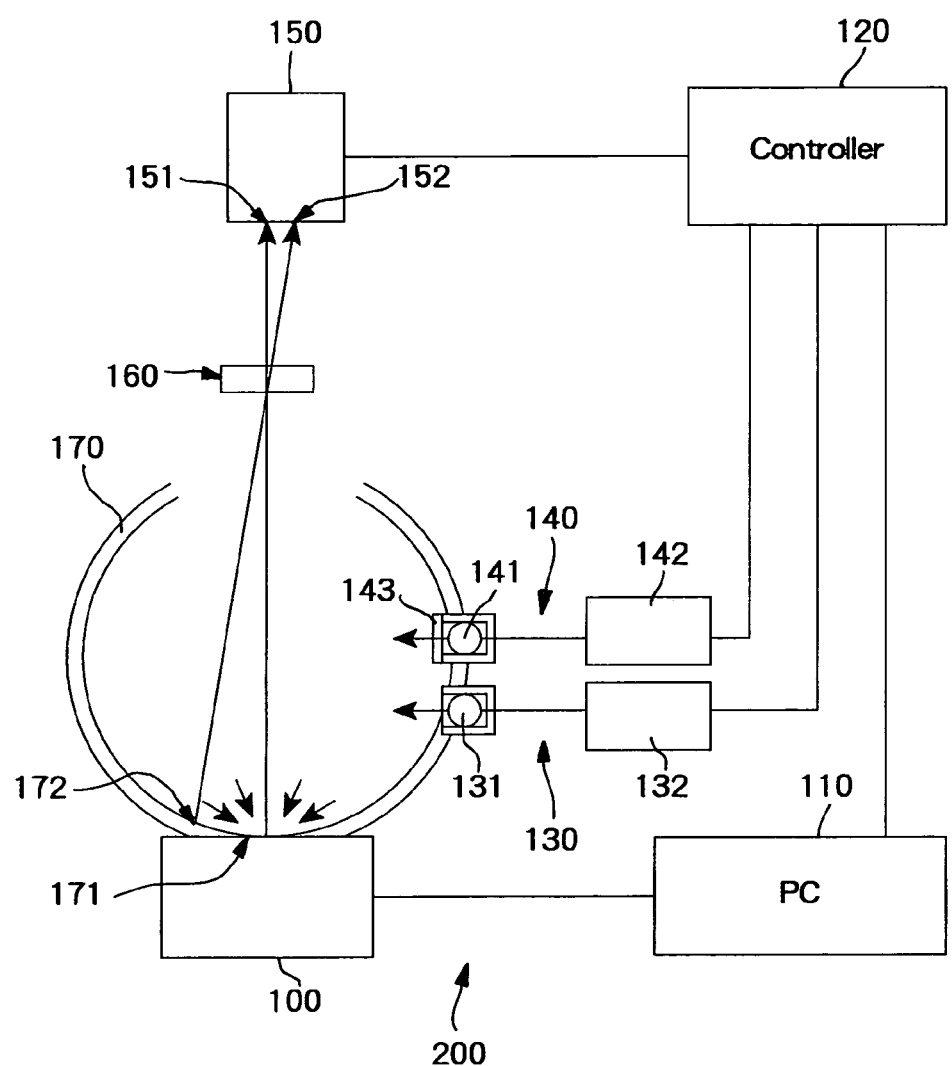
FIG. 7 illustrates the construction of an embodiment by applying the method of the present invention to a conventional measuring apparatus.
Figure 8:
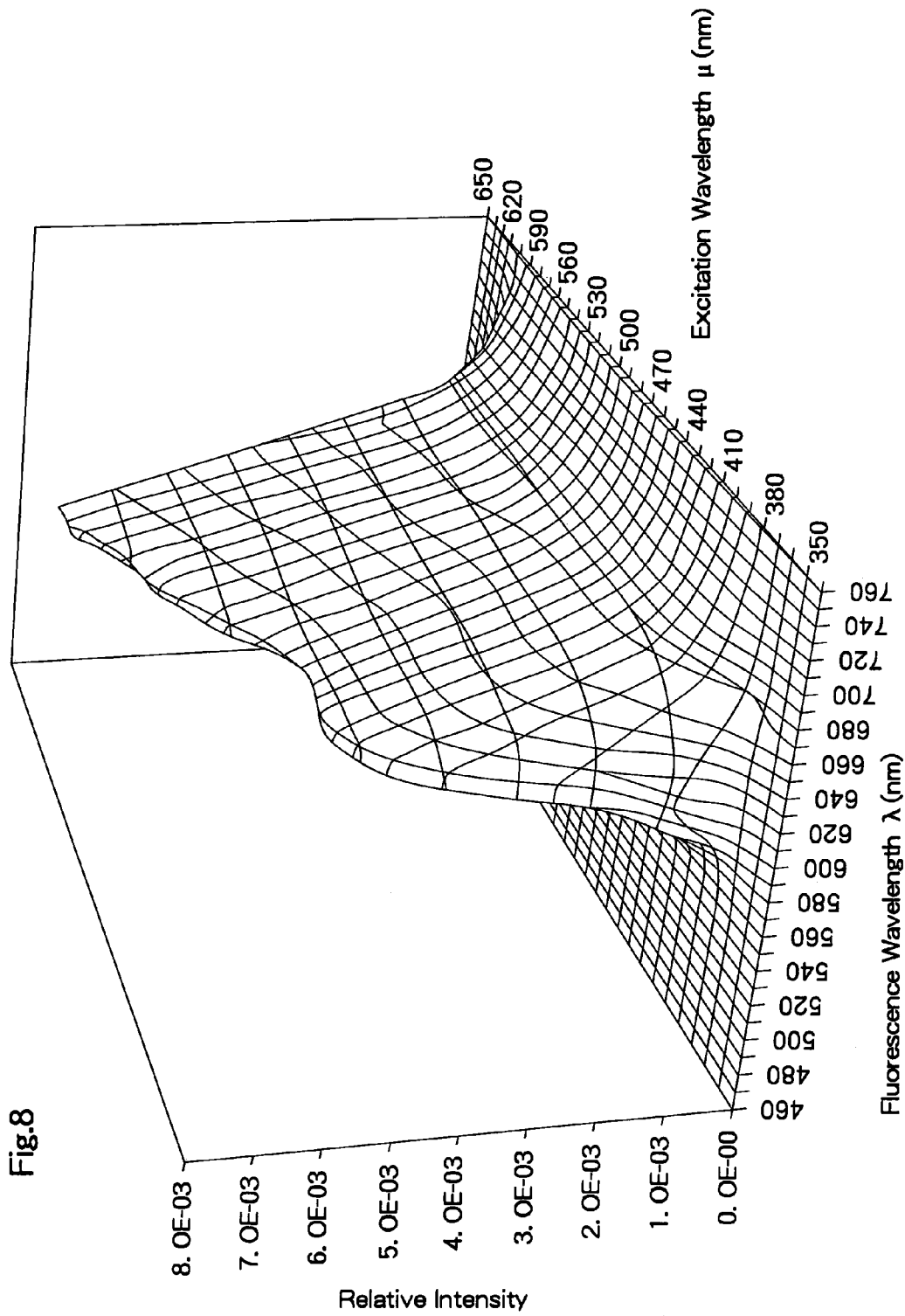
FIG. 8 shows an example of a bi-spectral luminescent radiance factor matrix.

Method of the embodiment is applicable to a conventional measuring apparatus of the method of U.S. Pat. No. 5,636,015 which synthesizes the virtual illumination light giving the same total spectral radiance factor as that given by the specified test illumination, if the spectral intensity of illumination light LA and LB and a bi-spectral luminescent radiance factor or a bi-spectral radiance factor close to the bi-spectral luminescent radiance factor or the bi-spectral radiance factor of the sample are known. FIG. 7 schematically shows an example of the embodiment applying the method of the present invention to measuring apparatus of the method of U.S. Pat. No. 5,636,015. A measuring apparatus 200 for measuring an optical property of a fluorescent sample is provided with a data processing means such as PC 110. PC 110 controls illuminators (first and second illuminator 130 and 140) and a spectral measurement means (spectral unit 150) via controller 120, receives the spectral intensity data of the illumination light and the light emitted from the sample, synthesizes the virtual illumination light, and calculates the total spectral radiance factor of the sample based on said data. The spectral intensity of the illumination light which isn't measured by the conventional apparatus 200 itself is measured by an additional measuring means for the spectral intensity of illumination light (spectral intensity unit 100). Spectral intensity unit 100 is arranged at the sample opening 171 and measures the spectral intensities of the illumination light LA and LB prior to sample measurement and sends data to PC 110. PC 110 synthesizes the illumination based on said measured spectral intensity data, the spectral intensity of the specified test illumination given as numerical data, and a bi-spectral luminescent radiance factor or a bi-spectral radiance factor close to either of the sample given as numerical data and calculates the total spectral radiance factor of the sample illuminated by the test illumination.

Controller 120, first illuminator 130, second illuminator 140, and spectral unit 150 in the measuring apparatus 200 in FIG. 7 respectively correspond to controller 7, first illuminator 2, second illuminator 3, and spectral unit 6 in FIG. 1 respectively. The light sources of both first and second illuminators 130 and 140 are Xe flash lamps having sufficient UV intensity, so that second illuminator 140 is further provided with a UV cutoff filter 143. First and second incident slits 151 and 152 of the spectral unit 150 respectively correspond to first and second incident slits 61 and 62 of dual channel spectral unit 6. Measuring apparatus 200 is further provided with receiving optics 160 and integrating sphere 170, inner wall of which are coated with highly diffusive and highly reflective white paint. Receiving optics 160 corresponds to receiving optics 5 in FIG. 1. Units 132 and 142 are drivers for lighting first and second illuminators 131 and 141 respectively. Integrating sphere 170 is provided with a sample opening 171 and a reference area 172 on the inner wall corresponding to reference plane 4 in FIG. 1.

The spectral sensitivity of the aforementioned spectral intensity unit 100 needs to cover wavelength range where said first and second illuminations contribute to the excitation and fluorescence of FWA (300 through 600 nm for example) and to be calibrated at least relatively. Although this embodiment replaces the unstable fluorescent standard by said spectral intensity unit 100, the procedure for synthesizing an illumination needs to be performed prior to sample measurement and accordingly, errors due to fluctuations of the illumination are not eliminated. This different embodiment is also applicable to a measuring apparatus of Gaertner-Griessers method. In this case, the colorimetric value (CIE whiteness for example) for the UV correction obtained by actually measuring the fluorescent standard in the conventional method is replaced by the value derived from the total spectral radiance factor calculated based on the spectral intensity of the illumination measured by said spectral intensity unit 100 and the bi-spectral luminescent radiance factor or the bi-spectral radiance factor for the sample. And the position of the UV cutoff filter in the apparatus is adjusted so that the calculated CIE whiteness matches the CIE whiteness also calculated based on the spectral intensity of the specified test illumination and said bi-spectral luminescent radiance factor or bi-spectral radiance factor. By applying the method of the present invention to the measuring apparatus of Gaertner-Griessers method, widely spread measuring apparatuses can be used without the unstable fluorescent standard which requires considerable cost and time, although the adjustment of UV filter is still required and the aforementioned several advantages of the method of the present invention are not provided.

In above mentioned embodiment, the weight $W(\lambda)$ isn't necessarily determined at each wavelength so that the total spectral radiance factor by the spectral intensity of the synthesized illumination matches the total spectral radiance factor by the spectral intensity of the specfied test illumination. Instead, the wavelength-independent weight can be determined so that the colorimetric value derived from the total spectral radiance factor by the synthesized illumination matches the value derived from the total spectral radiance factor by the test illumination.

Although the present invention has been fully described by way of examples with reference to the accompanying drawings, it is to be noted that various change and modifications will be apparent to those skilled in the art. Therefore, unless otherwise such changes and modifications depart from the scope of the present invention, they should be construed as being including therein.

What is claimed is:

1. A method for measuring an optical property of a fluorescent sample by obtaining a total spectral radiance factor of the sample illuminated by an illumination for testing, based on a predetermined bi-spectral radiance factor which is close to a bi-spectral radiance factor of the sample, a spectral intensity of the illumination for testing, spectral intensities of first and second illuminations which are different from each other, and measured spectral intensities of a light emitted from the sample illuminated by said first and second illuminations, said method comprising:

calculating a spectral radiance factor by said illumination for testing based on said predetermined bi-spectral radiance factor and said spectral intensity of said illumination for testing;

determining a first weight for said first illumination and a second weight for said second illumination so that a calculated spectral radiance factor by a synthesized illumination synthesized by combination of said first and second illuminations weighted by said first weight and said second weight respectively, based on said bi-spectral radiance factor and said spectral intensity of said synthesized illumination matches said spectral radiance factor by said illumination for testing;

calculating a spectral intensity of a light emitted from the sample illuminated by said synthesized illumination based on said measured spectral intensities and said first and second weights; and calculating said total spectral radiance factor of the sample illuminated by said illumination for testing based on said spectral intensity of said light emitted from the sample illuminated by said synthesized illumination and a spectral intensity of said synthesized illumination.

2. The method according to claim 1, wherein said bi-spectral radiance factor is a bi-spectral luminescent radiance factor.

3. The method according to claim 1, wherein said synthesized illumination is synthesized by linear combination of said first and second illuminations.

4. The method according to claim 1, further comprising calculating an effective bi-spectral radiance factor of the sample when including a fluorescent substrate and colorants based on said predetermined bi-spectral radiance factor which is close to a bi-spectral radiance factor of said substrate and one of 1) spectral transmittances of said colorants, and dot areas of said colorants amd superposition of said colorants in a measuring area and 2) spectral transmittances of said colorants and superposition of said colorants, and dot areas of said colorants and superposition of said colorants in said measuring area, for the measurement of the sample including said fluorescent substrate and said colorants.

5. The method according to claim 1, further comprising calculating an effective bi-spectral radiance factor of the sample when including a fluorescent substrate and colorants based on 1) said predetermined bi-spectral radiance factor of said substrate which is close to a bi-spectral radiance factor of said substrate; 2) bi-spectral radiance factors which are close to bi-spectral radiance factors of said substrate with said colorants and superposition of said colorants applied thereto; and 3) dot areas of said colorants and said superposition of said colorants in a measuring area, for the measurement of the sample including said fluorescent substrate and said colorants.

6. The method according to claim 1, wherein dot areas of colorants and superposition of said colorants are calculated based on at least one of measured total spectral radiance factors of the sample illuminated by said first and second illuminations.

7. The method according to claim 6, wherein said measured total spectral radiance factor for calculating dot areas of said colorants and said superposition of said colorants is measured by an illumination having a negligible intensity in UV region.

8. A method for measuring an optical property of a fluorescent sample by obtaining a total spectral radiance factor of the sample illuminated by an illumination for testing, based on a predetermined bi-spectral radiance factor which is close to a bi-spectral radiance factor of the sample, a spectral intensity of said illumination for testing, spectral intensities of first and second illuminations which are different from each other, and measured total spectral radiance factors of the sample illuminated by said first and second illuminations, said method comprising;

calculating a spectral radiance factor by said illumination for testing based-on said predetermined bi-spectral radiance factor and the spectral intensity of said illumination for testing;

calculating a first spectral radiance factor by said first illumination and a second spectral radiance factor by said second illumination based on said bi-spectral radiance factor and said spectral intensities of said first and second illuminations;

determining a first weight for said first illumination and a second weight for said second illumination so that a synthesized spectral radiance factor synthesized by combination of said first and second spectral radiance factors weighted by said first weight and said second weight, respectively, matches said spectral radiance factor by said illumination for testing; and calculating said total spectral radiance factor of the sample illuminated by said illumination for testing based on said measured total spectral radiance factors of the sample and said first and second weights.

9. The method according to claim 8, wherein said bi-spectral radiance factor is a bi-spectral luminescent radiance factor, and said first and second spectral radiance factors are each a fluorescent spectral radiance factor.

10. The method according to claim 8, wherein said synthesized spectral radiance factor is synthesized by linear combination of said first and second spectral radiance factors by said first and second illuminations, respectively.

11. The method according to claim 8, further comprising calculating an effective bi-spectral radiance factor of the sample when including a fluorescent substrate and colorants based said predetermined bi-spectral radiance factor which is close to a bi-spectral radiance factor of said substrate and one of 1) spectral transmittances of said colorants, and dot areas of said colorants and superposition of said colorants in a measuring area and 2) spectral transmittances of said colorants and superposition of said colorants, and dot areas of said colorants and superpositions of said colorants in said measuring area, for the measurement of the sample including said fluorescent substrate and said colorants.

12. The method according to claim 8, further comprising calculating an effective bi-spectral radiance factor of the sample when including a fluorescent substrate and colorants based on 1) said predetermined bi-spectral radiance factor of said substrate which is close to a bi-spectral radiance factor of said substrate; 2) bi-spectral radiance factors which are close to bi-spectral radiance factors of said substrate with said colorants and superposition of said colorants applied thereto; and 3) dot areas of said colorants and said superposition of said colorants in a measuring area, for the measurement of the sample including said fluorescent substrate and said colorants.

13. The method according to claim 8, wherein dot areas of colorants and superposition of said colorants are calculated based on at least one measured total spectral radiance factors of the sample illuminated by said first and second illuminations.

14. The method according to claim 13, wherein said measured total spectral radiance factor for calculating dot areas of said colorants and said superposition of said colorants is measured by an illumination having a negligible intensity in UV region.

15. An apparatus for measuring an optical property of a fluorescent sample comprising;
first and second illuminators for illuminating the sample by first and second illumination lights whose spectral intensities are different from each other;
a first spectral measurement unit for measuring a spectral intensity of light emitted from the sample;
a second spectral measurement unit for measuring said spectral intensities of said first and second illumination lights;
a storage for storing a predetermined bi-spectral radiance factor which is close to a bi-spectral radiance factor of the sample and a spectral intensity of an illumination for testing; and
a processor for consecutively turning on said first and second illuminators, for calculating total spectral radiance factors of the sample illuminated by said first and second illumination lights based on said spectral intensities of said first and second illumination lights measured by said second spectral measurement unit and said spectral intensity of said light emitted from the sample measured by said first spectral measurement unit, for calculating a spectral radiance factor of the sample illuminated by said illumination for testing based on said predetermined bi-spectral radiance factor and spectral intensity of said illlumination for testing, for calculating a first spectral radiance factor by said first illlumination and a second spectral radiance factor by said second illumination based on said predetermined bi-spectral radiance factor and said spectral intensities of said first and second illumination lights, for determining a first weight for said first illumination light and a second weight for said second illumination light so that a synthesized spectral radiance factor synthesized by combination of said first and second spectral radiance factors weighted by said first and said second weight, respectively, matches said spectral radiance factor by said illlumination for testing, and for calculating a total spectral radiance factor of the sample illuminated by said illumination for testing based on said total spectral radiance factors of the sample illluminated by said first and second illumination lights and said first and second weights.

16. The apparatus according to claim 15, wherein said storage further stores a predetermined bi-spectral radiance factor which is close to the bi-spectral radiance factor of a fluorescent substrate of the sample and spectral transmittances of colorants or spectral transmittances of said colorants and a superposition of said colorants applied on said fluorescent substrate, and stores dot areas of said colorants and said superposition of said colorants in measuring area, and
wherein said processor calculates an effective bi-spectral radiance factor of the sample based on said data stored in said stored in said storage for calculating said total spectral radiance factor of the sample illuminated by said illumination for testing.

17. The apparatus according to claim 15, wherein said storage further stores a predetermined bi-spectral radiance factor which is close to a bi-spectral radiance factor of a fluorescent substrate of the sample and bi-spectral radiance factors which are close to bi-spectral radiance factors of said fluorescent substrate, with said colorants and a superposition of said colorants applied thereto, and dot areas of said colorants and said superposition of said colorants in a measuring area, and
wherein said processor calculates an effective bi-spectral radiance factor of the sample based on said data stored in said storage for calculating said total spectral radiance factor of the sample illuminated by said illumination for testing.

18. The apparatus according to claim 15, wherein said processor calculates dot areas of colorants and a superposition of said colorants based on at least one of said total spectral radiance factors of the sample illuminated by said first and second illuminations.

19. The apparatus according to claim 18, wherein said total spectral radiance factor for calculating dot areas of said colorants and said superposition of said colorants is measured by an illumination having the negligible intensity in UV region.

20. The apparatus according to claim 19, wherein said first illuminator comprises one or more incandescent lamps and said second illuminator comprises one or more UV LED's.

21. The apparatus according to claim 20, wherein said first illumination light is provided by said first illuminator and said second illumination light is provided by both said first and second illuminators.

22. The apparatus according to claim 15, wherein said first and second illumination lights have negligible UV intensities out of a measuring wavelength range of said spectral measurement unit for illumination light.

23. An apparatus for measuring an optical property of a fluorescent sample comprising;

first and second illuminators for illuminating the sample by first and second illumination lights whose spectral intensities are different from each other;

a first spectral measurement unit for measuring a spectral intensity of light emitted from the sample;

a second spectral measurement unit for measuring said spectral intensities of said first and second illumination lights;

a storage for storing a predetermined bi-spectral radiance factor which is close to a bi-spectral radiance factor of the sample and a spectral intensity of an illlumination for testing; and a processor for consecutively turning on said first and second illuminators, for calculating a spectral radiance factor of the sample illluminated by said illumination for testing based on said predetermined bi-spectral radiance factor and said spectral intensity of said illumination for testing, for determining a first weight for said first illumination light and a second weight of said second illumination ight so that a calculated spectral radiance factor by a synthesized illumination synthesized by combination of measured spectral intensities of said first and second illumination lights weighted by said first and second weights respectively, based on said predetermined bi-spectral radiance factor and said spectral intensity of said synthesized illumination, matches said spectral radiance factor by said illumination for testing, for calculating a spectral intensity of a light emitted from the sample illuminated by said synthesized illumination based on measured spectral intensities of lights emitted from the sample and said first and second weights, and for calculating a total spectral radiance factor of the sample illuminated by said illumination for testing based on said spectral intensity of said light emitted from the sample illuminated by said synthesized illumination and said spectral intensity of said synthesized illumination.

* * * * *

UNITED STATES PATENT AND TRADEMARK OFFICE
CERTIFICATE OF CORRECTION

PATENT NO. : 7,502,099 B2
APPLICATION NO. : 11/398911
DATED : March 10, 2009
INVENTOR(S) : Kenji Imura It is certified that error appears in the above-identified patent and that said Letters Patent is hereby corrected as shown below:

In the Claims

Column 27, claim 13, line 35, before "measured total spectral" insert --of said--.

Column 28, claim 15, line 11, before "and said second weight" insert --weight--.

Column 28, claim 15, line 12, after "factor by said" delete "illlumination" and substitute --illumination-- in its place.

Column 28, claim 15, line 16, before "by said first" delete "illluminated" and substitute --illuminated-- in its place.

Column 29, claim 23, line 11, after "spectral intensity of an" delete "illlumination" and substitute --illumination-- in its place.

Column 29, claim 23, line 15, after "of the sample" delete "illluminated" and substitute --illuminated-- in its place.

Signed and Sealed this

Second Day of February, 2010

David J. Kappos
*Director of the United States Patent and Trademark Office*